(12) United States Patent
Nakamura

(10) Patent No.: US 11,460,676 B2
(45) Date of Patent: Oct. 4, 2022

(54) OBJECTIVE OPTICAL SYSTEM AND ENDOSCOPE

(71) Applicant: OLYMPUS CORPORATION, Hachioji (JP)

(72) Inventor: Minoru Nakamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 199 days.

(21) Appl. No.: 16/922,038

(22) Filed: Jul. 7, 2020

(65) Prior Publication Data

US 2020/0333568 A1 Oct. 22, 2020

Related U.S. Application Data

(63) Continuation of application No. PCT/JP2018/031711, filed on Aug. 28, 2018.

(30) Foreign Application Priority Data

Feb. 27, 2018 (JP) .............................. JP2018-032787

(51) Int. Cl.
*G02B 13/04* (2006.01)
*G02B 9/12* (2006.01)
(Continued)

(52) U.S. Cl.
CPC .......... *G02B 13/04* (2013.01); *A61B 1/00163* (2013.01); *G02B 7/04* (2013.01); *G02B 9/12* (2013.01); *A61B 1/04* (2013.01)

(58) Field of Classification Search
CPC . G02B 13/04; G02B 7/04; G02B 9/12; G02B 23/243; G02B 9/60; G02B 9/01;
(Continued)

(56) References Cited

U.S. PATENT DOCUMENTS

| 8,203,798 B2 | 6/2012 | Takato |
| 8,456,767 B2 | 6/2013 | Takato |

(Continued)

FOREIGN PATENT DOCUMENTS

| JP | 4819969 B2 | 9/2011 |
| JP | 2017209154 A | 11/2017 |

(Continued)

OTHER PUBLICATIONS

Japanese Office Action (and English language translation thereof) dated Jan. 27, 2021 issued in Japanese Application No. 2020-502790.

(Continued)

*Primary Examiner* — Marin Pichler
(74) *Attorney, Agent, or Firm* — Holtz, Holtz & Volek PC

(57) ABSTRACT

An objective optical system includes in order from an object side to an image side, a first lens group having a negative refractive power, a second lens group, and a third lens group having a positive refractive power. At a time of focusing, the second lens group moves in an optical axial direction. The third lens group includes, from the object side to the image side, a front group and a rear group. The front group includes a cemented lens having a positive refractive power or includes a single lens having a positive refractive power. The rear group includes a cemented lens having a positive refractive power, and the following conditional expression (1) is satisfied:

$$0.45 < d3t/f32 < 0.8 \qquad (1).$$

8 Claims, 17 Drawing Sheets

(51) Int. Cl.
*G02B 7/04* (2021.01)
*A61B 1/00* (2006.01)
*A61B 1/04* (2006.01)

(58) Field of Classification Search
CPC ... G02B 9/18; G02B 9/20; G02B 9/22; G02B 9/24; G02B 9/26; G02B 13/0035; G02B 13/004; G02B 13/0045; G02B 13/005; G02B 15/143; G02B 15/1435; G02B 15/143501; G02B 15/143503; G02B 15/143505; G02B 15/143507; G02B 21/00–368; G02B 25/00; G02B 25/001; G02B 9/34; G02B 15/144507; G02B 15/144511; G02B 15/144513; G02B 15/144515; G02B 9/62; A61B 1/00163; A61B 1/04; A61B 1/05; A61B 1/00096; A61B 1/00188
USPC ........ 359/682, 689–690, 748, 753, 784–792, 359/368–398, 643–647, 656–661; 600/101–183
See application file for complete search history.

(56) References Cited

U.S. PATENT DOCUMENTS

| | | | |
|---|---|---|---|
| 8,773,765 | B2 | 7/2014 | Sasamoto |
| 9,106,848 | B2 | 8/2015 | Kamo |
| 9,459,443 | B2 | 10/2016 | Uzawa et al. |
| 9,568,726 | B2 | 2/2017 | Kamo et al. |
| 10,101,575 | B2 | 10/2018 | Katakura |
| 2011/0211267 | A1 | 9/2011 | Takato |
| 2012/0057251 | A1 | 3/2012 | Takato |
| 2013/0155212 | A1 | 6/2013 | Kamo |
| 2013/0217965 | A1 | 8/2013 | Sasamoto |
| 2015/0042773 | A1 | 2/2015 | Uzawa et al. |
| 2015/0268460 | A1* | 9/2015 | Takada ............ G02B 13/04 359/738 |
| 2016/0154230 | A1 | 6/2016 | Katakura |
| 2016/0327780 | A1 | 11/2016 | Kamo et al. |
| 2017/0351059 | A1* | 12/2017 | Gyoda ............ G02B 9/12 |
| 2018/0196241 | A1* | 7/2018 | Shibayama ........ G02B 9/60 |
| 2018/0373018 | A1 | 12/2018 | Katakura |
| 2019/0025568 | A1 | 1/2019 | Matsuura |

FOREIGN PATENT DOCUMENTS

| | | |
|---|---|---|
| WO | 2010119640 A1 | 10/2010 |
| WO | 2011070930 A1 | 6/2011 |
| WO | 2012169369 A1 | 12/2012 |
| WO | 2013021744 A1 | 2/2013 |
| WO | 2014129089 A1 | 8/2014 |
| WO | 2015025843 A1 | 2/2015 |
| WO | 2015194311 A1 | 12/2015 |
| WO | 2017179373 A1 | 10/2017 |
| WO | 2017183371 A1 | 10/2017 |

OTHER PUBLICATIONS

International Search Report (ISR) (and English translation thereof) dated Dec. 4, 2018 issued in International Application No. PCT/JP2018/031711.

Written Opinion dated Dec. 4, 2018 issued in International Application No. PCT/JP2018/031711.

International Preliminary Report on Patentability (IPRP) (and English language translation thereof) dated Aug. 27, 2020 issued in International Application No. PCT/JP2018/031711.

* cited by examiner

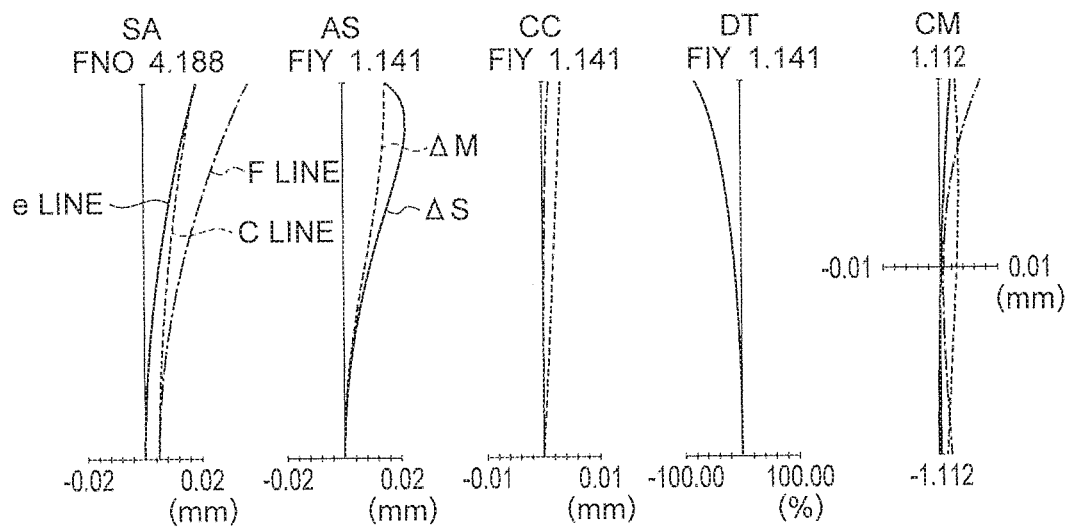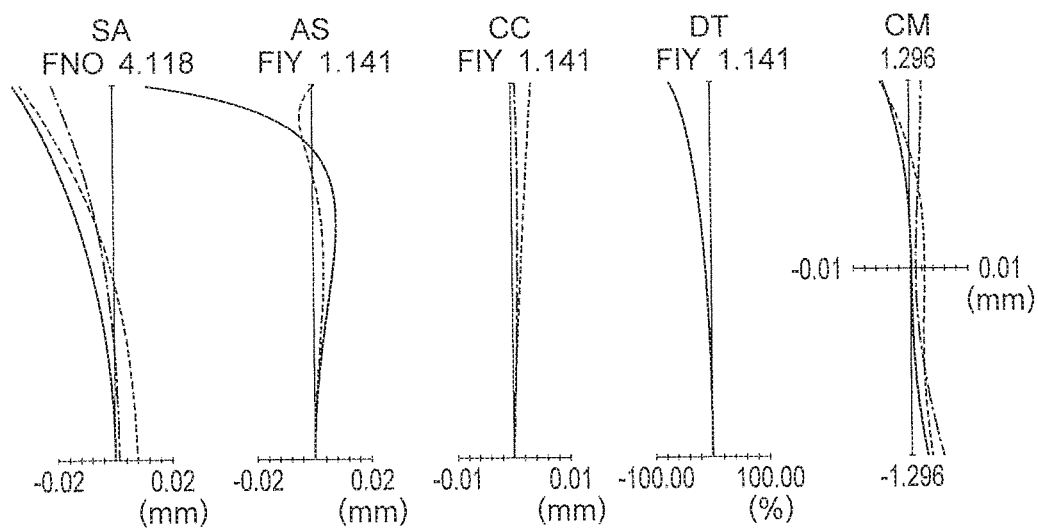

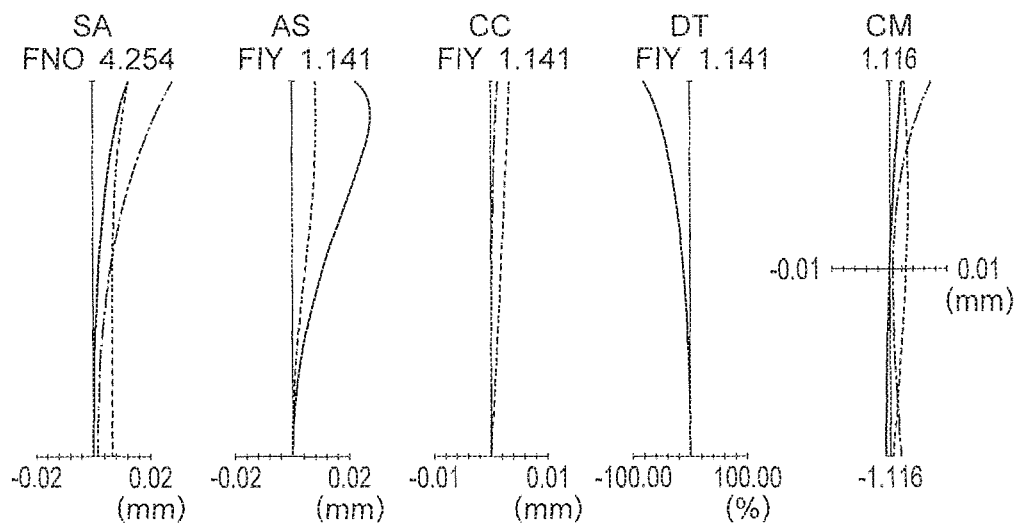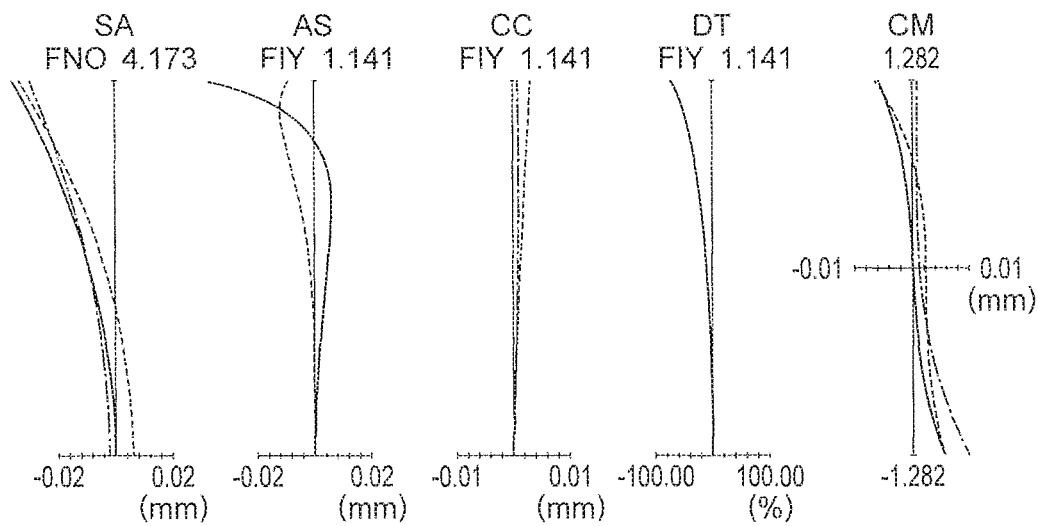

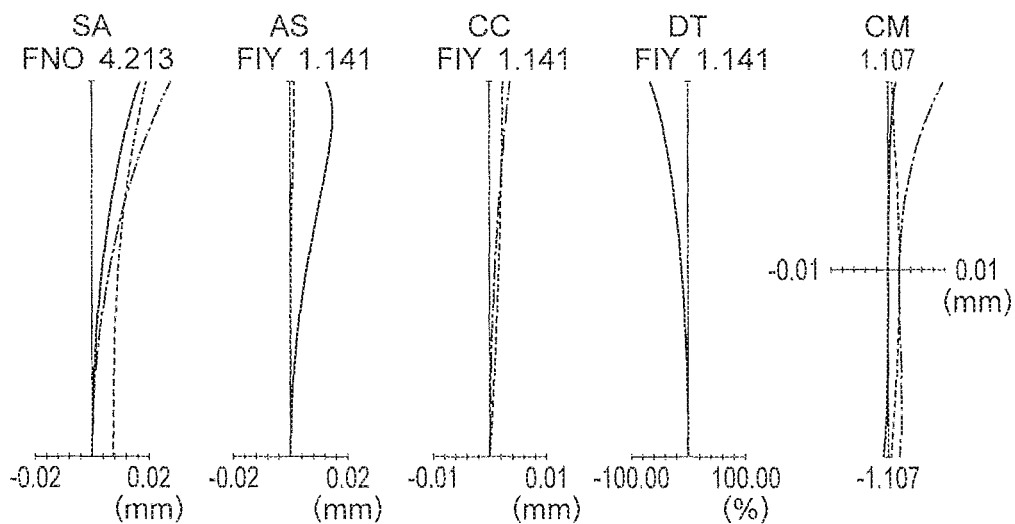
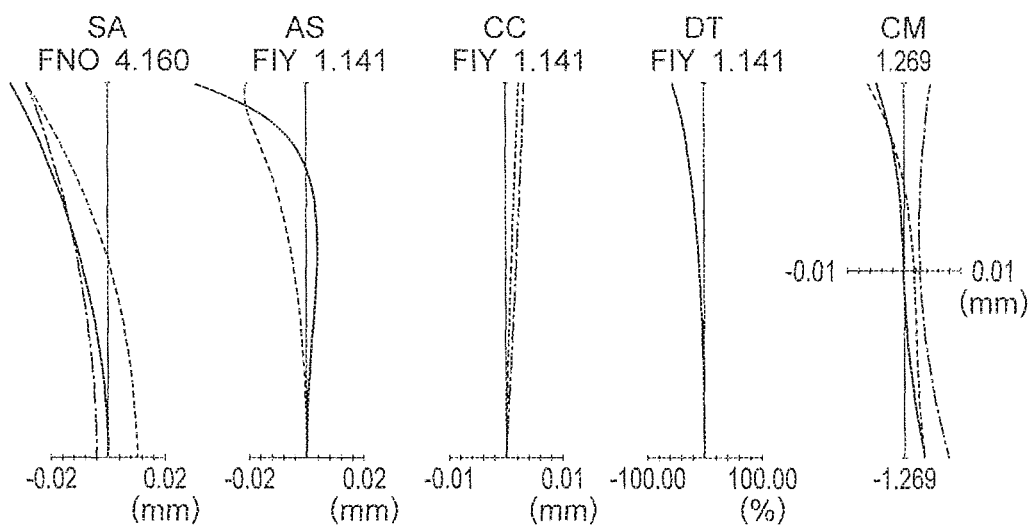

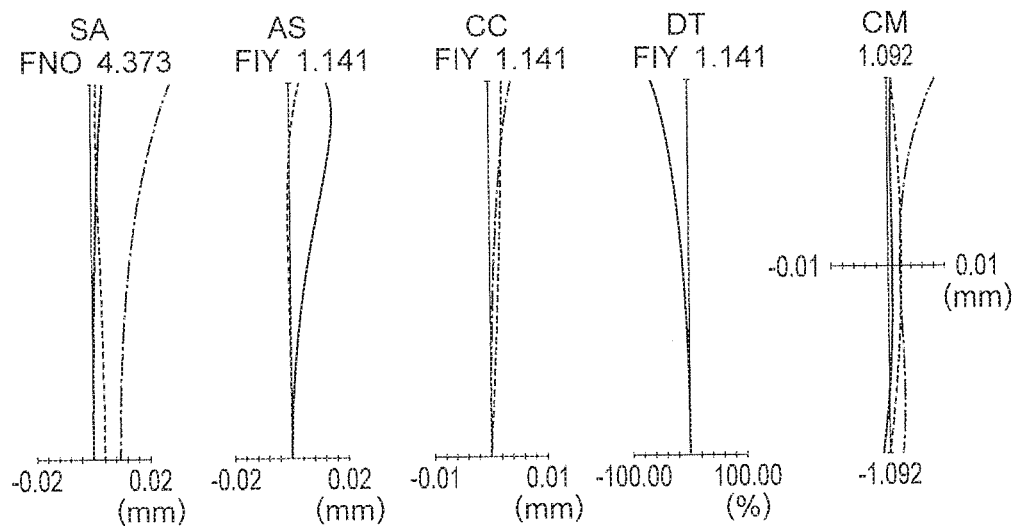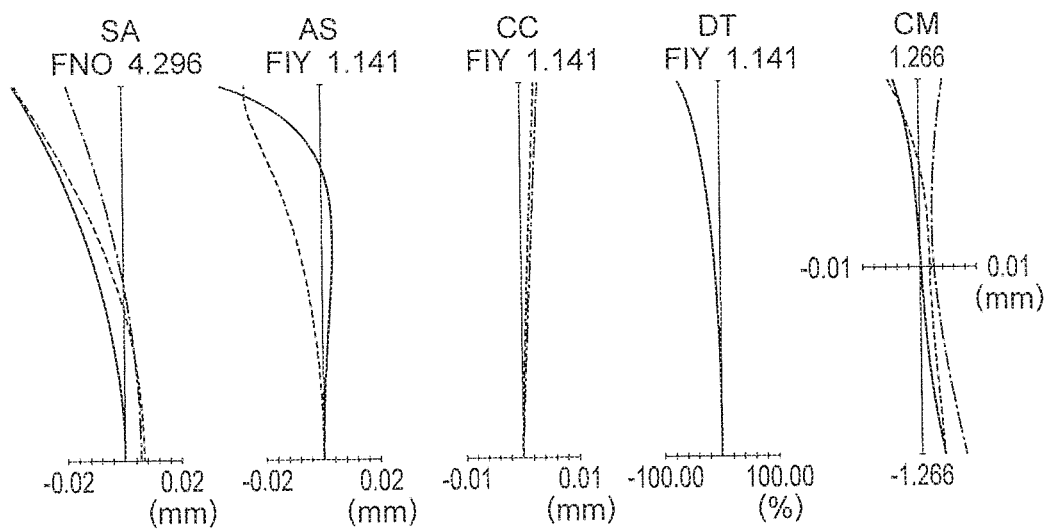

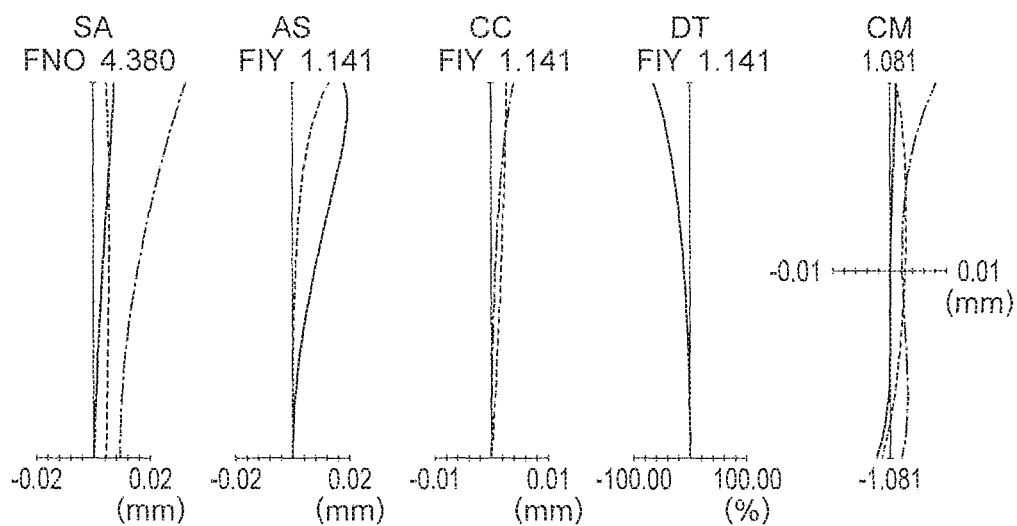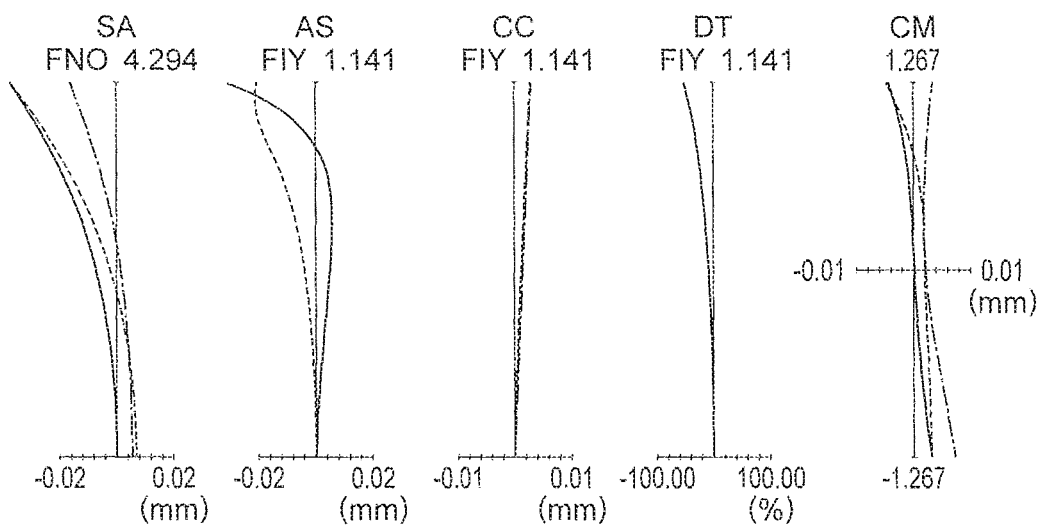

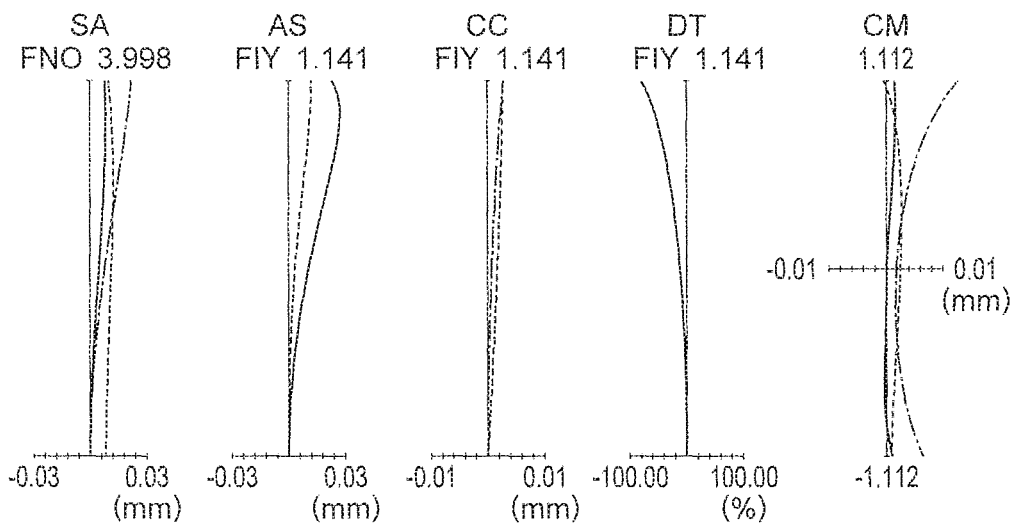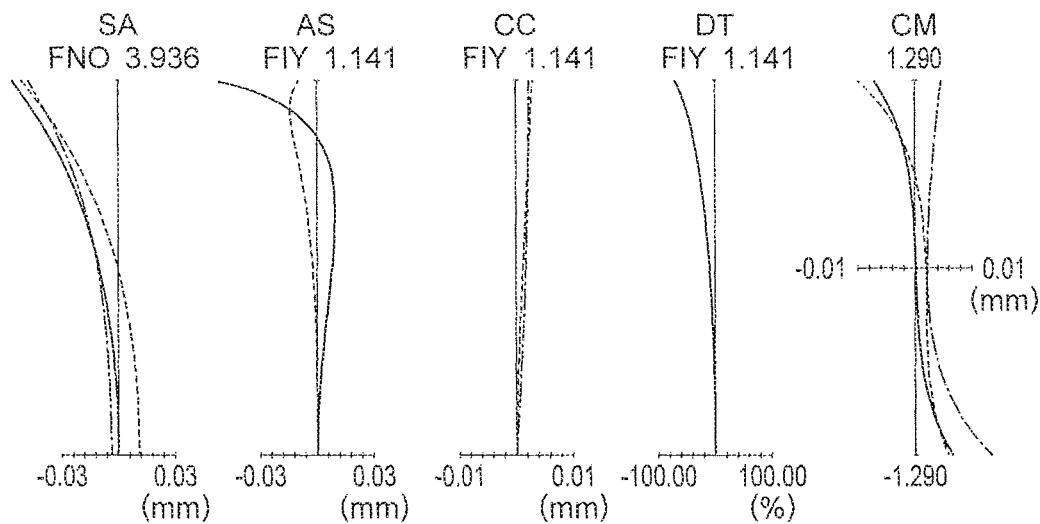

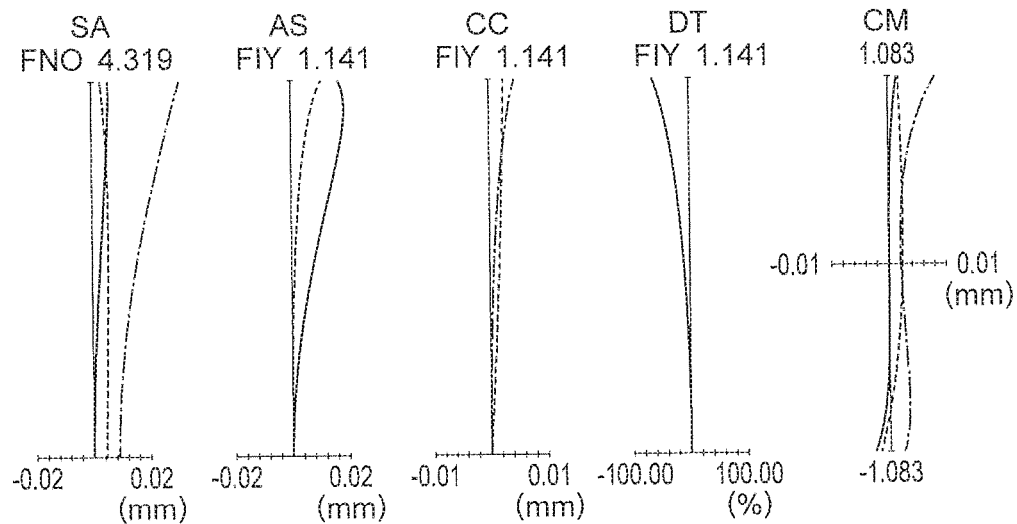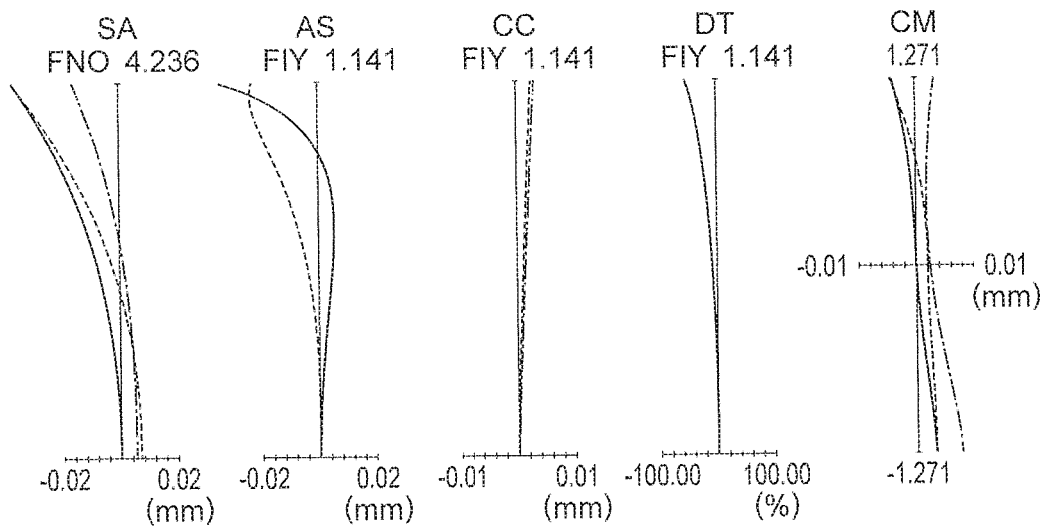

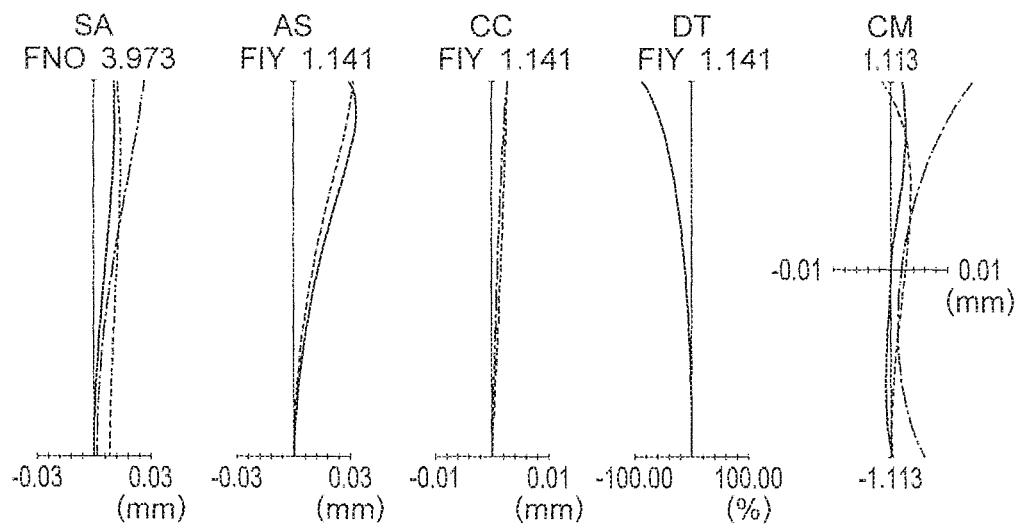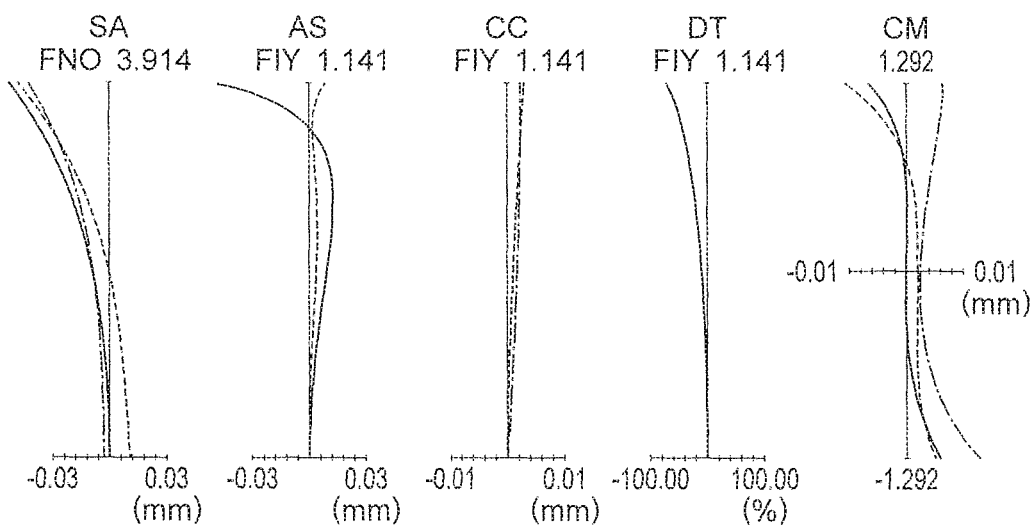

OBJECTIVE OPTICAL SYSTEM AND ENDOSCOPE

CROSS-REFERENCE TO RELATED APPLICATION

The present application is a continuation application of PCT/JP2018/031711 filed on Aug. 28, 2018 which is based upon and claims the benefit of priority from Japanese Patent Application No. 2018-032787 filed on Feb. 27, 2018; the entire contents of which are incorporated herein by reference.

BACKGROUND

Technical Field

The present disclosure relates to an objective optical system and an endoscope.

In medical endoscopes, magnifying observation is used for observation of a lesion part. For carrying out the magnifying observation of the lesion part, it is necessary to find the lesion part. In the magnifying observation, compared to conventional observation (hereinafter, referred to as 'normal observation') an observation range is narrow. Consequently, it is not easy to find the lesion part in the magnifying observation. For such reason, it is desirable that the normal observation and the magnifying observation be possible by one objective optical system.

In the magnifying observation, a distance from an objective optical system up to an object position (hereinafter, referred to as 'object distance') is about 3 mm for example. Whereas, in the normal observation, the object distance is much longer than 3 mm.

When an optical system is arranged in order that the object position at the time of the normal observation and a focusing position of an objective optical system coincide, an object image in the normal observation (hereinafter, referred to as 'normal image') becomes a focused image.

Whereas, an object position at the time of magnifying observation is far away from the object position at the time of normal observation. Moreover, the object position at the time of magnifying observation is not included in a depth of field of the objective optical system at the time of normal observation. Consequently, in an optical system in which the normal image is focused, the object image in the magnifying observation (hereinafter, referred to as 'magnified image') does not become a focused image.

For forming a focused object image even in the magnifying observation, a focus function is to be imparted to the objective optical system. By the objective optical system having the focus function, it is possible to form both the normal image and the magnified image in a focused state.

Objective optical systems having the focus function are disclosed in Japanese Patent No. 4819969 Publication and International Unexamined Patent Application Publication No. 2015/025843 (Example 7). The objective optical systems include a first lens group having a negative refractive power, a second lens group having a positive refractive power, and a third lens group having a positive refractive power. Only the second lens group moves at the time of focusing.

In the normal observation and the magnifying observation, it is preferable that a lesion part could be observed in more detail. For being able to observe the lesion part in more detail, an F-number of an objective optical system is to be made small. However, as the F-number of the optical system is made small, the depth of field becomes narrow. Consequently, in both the normal observation and the magnifying observation, a focusing range in an optical-axial direction becomes narrow.

As a method of widening the focusing range in the optical-axial direction, for example, there is a method of generating an image having a large depth of field by combining two images having different focusing positions. For acquiring two images having different focusing positions, it is necessary to form two optical images having different focusing positions.

For instance, by disposing a prism which forms two optical paths in an optical path of an objective optical system, it is possible to form two optical images. By making a length of one optical path and a length of the other optical path differ, it is possible to form two optical images with different focusing positions. The prism is to be disposed between a lens positioned nearest to image and an image sensor. Therefore, it is desirable that the objective optical system have an adequate back focus.

SUMMARY

An objective optical system according to at least some embodiments of the present disclosure includes in order from an object side to an image side:

a first lens group having a negative refractive power,
a second lens group, and
a third lens group having a positive refractive power, wherein at a time of focusing, the second lens group moves in an optical axial direction, the third lens group includes, from the object side to the image side, a front group and a rear group, the front group includes a cemented lens having a positive refractive power or includes a single lens having a positive refractive power, the rear group includes a cemented lens having a positive refractive power, and the following conditional expression (1) is satisfied:

$$0.45 < d3t/f32 < 0.8 \tag{1},$$

where, d3t denotes a distance on an optical axis from a lens surface positioned nearest to an object in the front group up to a lens surface positioned nearest to the object in the rear group, and f32 denotes a focal length of the rear group.

Moreover, an endoscope according to a least some embodiments of the present disclosure includes:

the abovementioned objective optical system, and
an image sensor.

BRIEF DESCRIPTION OF THE DRAWINGS

FIG. 3A, FIG. 3B, FIG. 3C, FIG. 3D, FIG. 3E, FIG. 3F, FIG. 3G, FIG. 3H, FIG. 3I, and FIG. 3J are aberration diagrams of the objective optical system of the example 1;

FIG. 5A, FIG. 5B, FIG. 5C, FIG. 5D, FIG. 5E, FIG. 5F, FIG. 5G, FIG. 5H, FIG. 5I, and FIG. 5J are aberration diagrams of the objective optical system of the example 2;

FIG. 7A, FIG. 7B, FIG. 7C, FIG. 7D, FIG. 7E, FIG. 7F, FIG. 7G, FIG. 7H, FIG. 7I, and FIG. 7J are aberration diagrams of the objective optical system of the example 3;

FIG. 9A, FIG. 9B, FIG. 9C, FIG. 9D, FIG. 9E, FIG. 9F, FIG. 9G, FIG. 9H, FIG. 9I, and FIG. 9J are aberration diagrams of the objective optical system of the example 4;

FIG. 11A, FIG. 11B, FIG. 11C, FIG. 11D, FIG. 11E, FIG. 11F, FIG. 11G, FIG. 11H, FIG. 11I, and FIG. 11J are aberration diagrams of the objective optical system of the example 5;

FIG. 13A, FIG. 13B, FIG. 13C, FIG. 13D, FIG. 13E, FIG. 13F, FIG. 13G, FIG. 13H, FIG. 13I, and FIG. 13J are aberration diagrams of the objective optical system of the example 6;

FIG. 15A, FIG. 15B, FIG. 15C, FIG. 15D, FIG. 15E, FIG. 15F, FIG. 15G, FIG. 15H, FIG. 15I, and FIG. 15J are aberration diagrams of the objective optical system of the example 7;

FIG. 17A, FIG. 17B, FIG. 17C, FIG. 17D, FIG. 17E, FIG. 17F, FIG. 17G, FIG. 17H, FIG. 17I, and FIG. 17J are aberration diagrams of the objective optical system of the example 8.

DETAILED DESCRIPTION

Figure 1A:
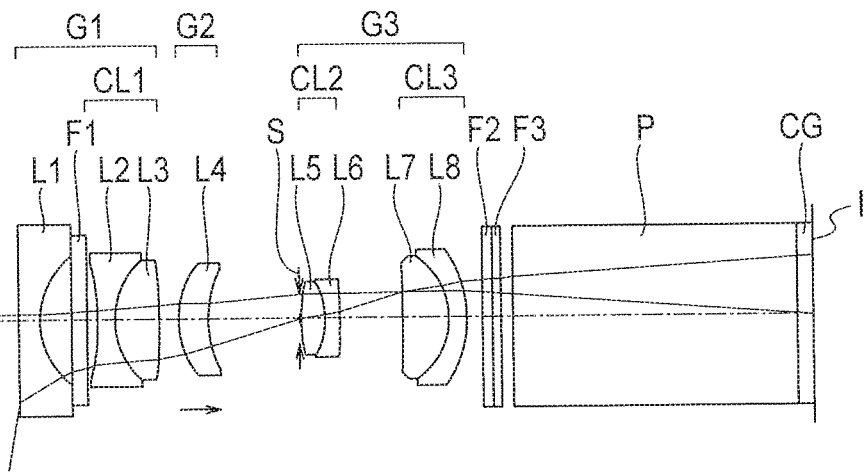
FIG. 1A, FIG. 1B, and FIG. 1C are cross-sectional views showing specific arrangements of an objective optical system of the present embodiment, and a specific arrangement of a prism.

An objective optical system and an endoscope according to the present embodiments will be described below in detail by referring to the accompanying diagrams. However, the present disclosure is not restricted to the embodiments described below.

An objective optical system according to the present embodiment, in an endoscopic observation, enables to carry out a normal observation and a magnifying observation with one optical system. For this, in the objective optical system according to the present embodiment, the optical system includes a plurality of lens groups, and one lens group moves on an optical axis.

Accordingly, the normal observation is possible when focused to an object at a long distance, and the magnifying observation is possible when focused to an object at a short distance. An object distance for the object at the long distance is longer than an object distance for the object at the short distance. In the magnifying observation, an observation with a magnification higher than that in the normal observation is possible.

A basic arrangement of the objective optical system of the present embodiment will be described below. In the basic arrangement, the objective optical system includes in order from an object side to an image side, a first lens group having a negative refractive power, a second lens group, and a third lens group having a positive refractive power, and at a time of focusing, the second lens group moves in an optical-axial direction. The third lens group includes, from the object side to the image side, a front group and a rear group, the front group includes a cemented lens having a positive refractive power or includes a single lens having a positive refractive power, and the rear group includes a cemented lens having a positive refractive power.

In the basic arrangement, the objective optical system includes in order from the object side to the image side, the first lens group having a negative refractive power, the second lens group, and the third lens group having a positive refractive power. By making such arrangement, it is possible to secure a wide angle of view, and to shorten an overall length of the optical system.

At the time of the normal observation and the magnifying observation, an object distance differs. In an observation of an object, it is preferable to form a sharp image even when the object distance changes. For this, it is necessary to move at least one lens group.

It is preferable that the number of lens groups to be moved be small. When the number of lens group to be moved is one, it is possible to simplify a drive mechanism. As mentioned above, in the basic arrangement, the second lens group moves at the time of focusing. The number of lens groups that move being one, it is possible to simplify the drive mechanism. It is preferable that the first lens group and the third lens group be fixed all the time.

When the object distance changes, an astigmatic difference varies. For a sharp image to be formed, the variation in the astigmatic difference has to be suppressed. As mentioned above, as the object distance changes, the second lens group moves. By the second lens group being moves, the astigmatic difference varies even in the second lens group.

In the basic arrangement, the astigmatic difference in the second lens group occurs in an opposite direction of a direction of variation of the astigmatic difference in the first lens group. An amount of variation of the astigmatic difference in the second lens group is almost same as an amount of variation in the astigmatic difference in the first lens group. Therefore, it is possible to cancel the variation in the astigmatic difference in the first lens group by the astigmatic difference in the second lens group.

In such manner, it is possible to suppress the variation in the astigmatic difference by the first lens group and the second lens group. However, for a sharp image to be formed, it is preferable that the variation in aberration other than the astigmatic difference, such as a variation in a spherical aberration, a variation in a coma, and a variation in a chromatic aberration has been suppressed.

Moreover, the variation in the spherical aberration, the variation in the coma, and the variation in the chromatic aberration are susceptible to occur in the first lens group and the second lens group. In the basic arrangement, it is possible to make small each of the variation in aberration. Consequently, as the optical system as a whole, it is possible to suppress each of the variation in aberration.

For a sharp image to be formed, it is important not only to suppress the variation in aberration, but also to make an aberration amount small. For making the aberration amount small, an occurrence amount of aberration is to be suppressed or an aberration is to be corrected favorably in the overall optical system.

It is not possible to correct favorably the spherical aberration, the coma, and the chromatic aberration only by the first lens group and the second lens group. It is possible to correct these aberrations favorably by the third lens group.

The third lens group includes in order from the object side to the image side, the front group and the rear group. The front group includes the cemented lens having a positive refractive power or includes the single lens having the positive refractive power, and the rear group includes the cemented lens having a positive refractive power.

A height of an axial light ray is high at a position of the front group. Therefore, at the front group, it is possible to correct the spherical aberration favorably. A height of an off-axis light ray is high at a position of the rear group. Therefore, at the rear group, it is possible to correct the coma and an astigmatism favorably. Moreover, since the cemented lens is used in the rear group, it is possible to correct a chromatic aberration of magnification favorably by the cemented lens.

The front group includes the cemented lens or includes the single lens. By using the cemented lens or the single lens, it is possible to correct the spherical aberration favorably. When the cemented lens is used in the front group, it is possible to correct favorably a longitudinal chromatic aberration in addition to the spherical aberration.

In such manner, in the front group of the third lens group, it is possible to correct mainly a longitudinal aberration favorably, and in the rear group of the third lens group, it is possible to correct an off-axis aberration favorably. Moreover, it is possible to secure a wide focusing range, to secure an adequate back focus, and to shorten the overall length of the optical system.

In the front group, one cemented lens is to be disposed or one single lens is to be disposed. One cemented lens is to be disposed in the rear group. By making such arrangement, it is possible to make small the number of lenses in the third lens group.

In an optical system at the time of normal observation, the coma occurs substantially in the second lens group. On the other hand, the coma occurs in the third lens group as well. The coma in the third lens group occurs in a direction opposite to a direction in which the coma in the second lens group occurs.

An occurrence amount of the coma in the second lens group is larger than an occurrence amount of the coma in the third lens group. Therefore, it is not possible to correct the coma occurred in the second lens group only by the third lens group.

The coma occurs even in the first lens group. The coma which occurs in the first lens group occurs in a direction opposite to the direction in which the coma occurs in the second lens group. In other words, the coma which occurs in the first lens group occurs in a direction same as the direction in which the coma in the third lens group occurs. Therefore, it is possible to correct the coma in the second lens group by the first lens group and the third lens group.

Figure 1B:
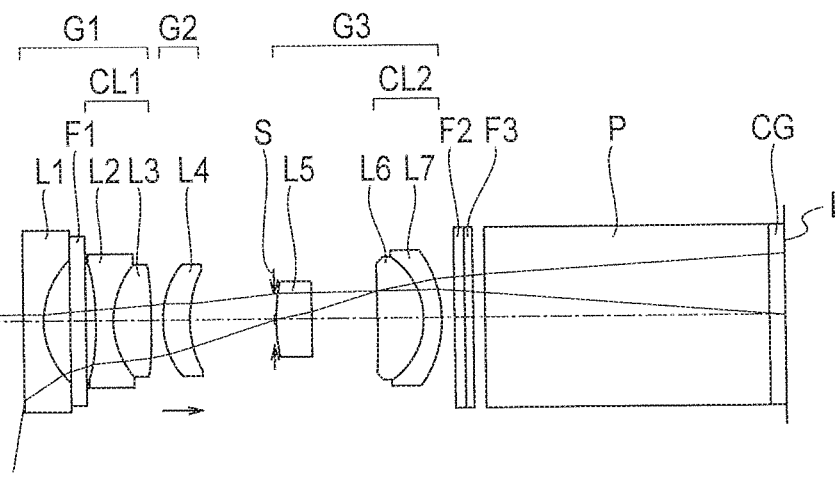
Figure 1C:
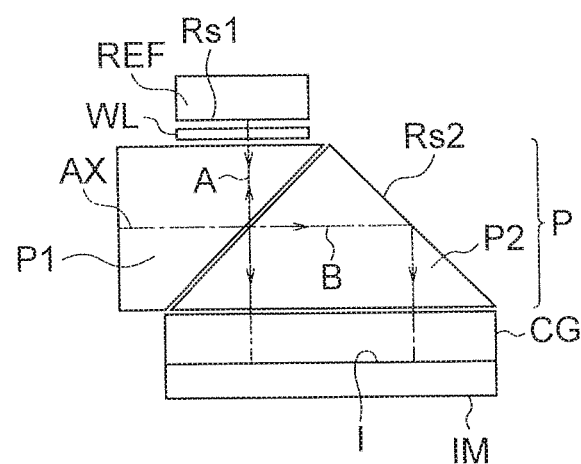
Figure 2A:
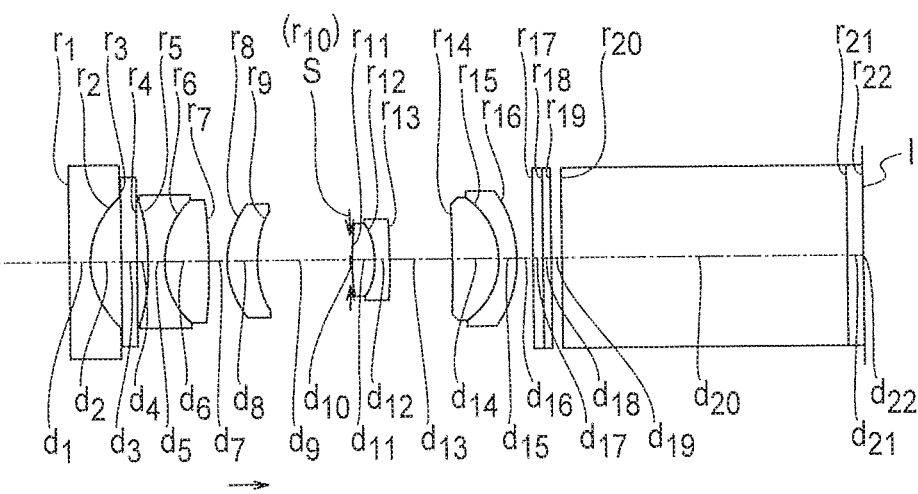
FIG. 2A and FIG. 2B are cross-sectional views of an objective optical system of an example 1.
Figure 2B:
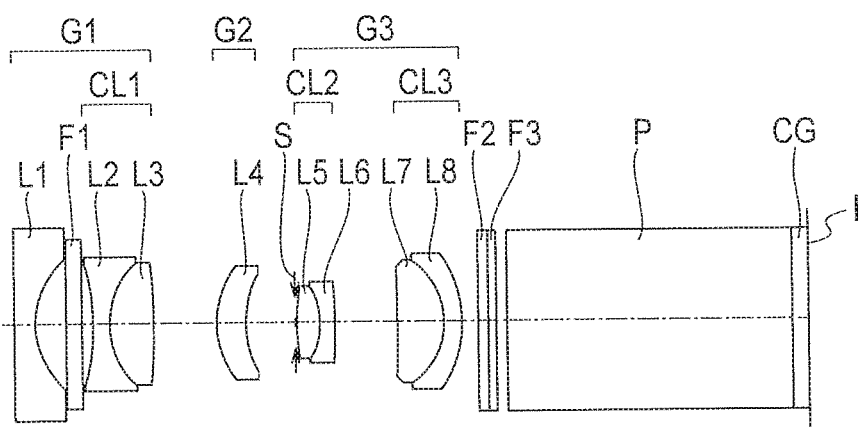
Figure 4A:
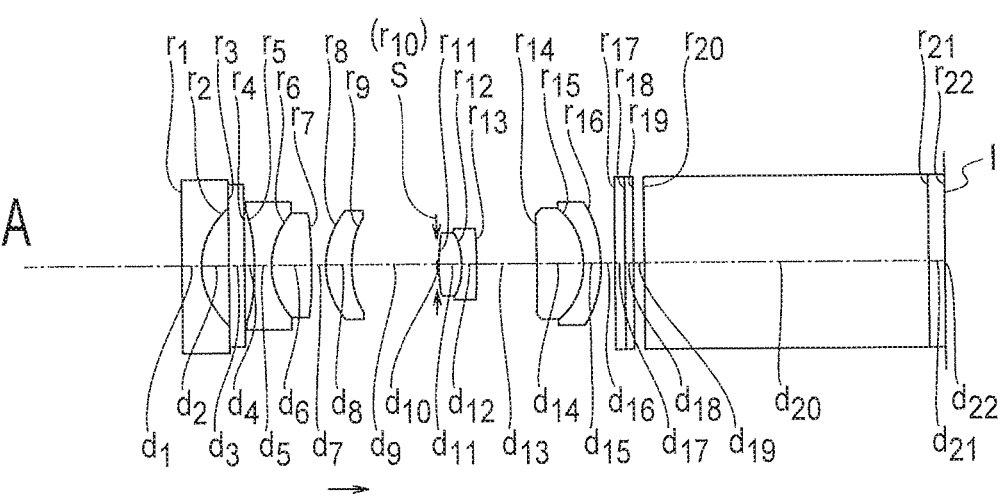
FIG. 4A and FIG. 4B are cross-sectional views of an objective optical system of an example 2.
Figure 4B:
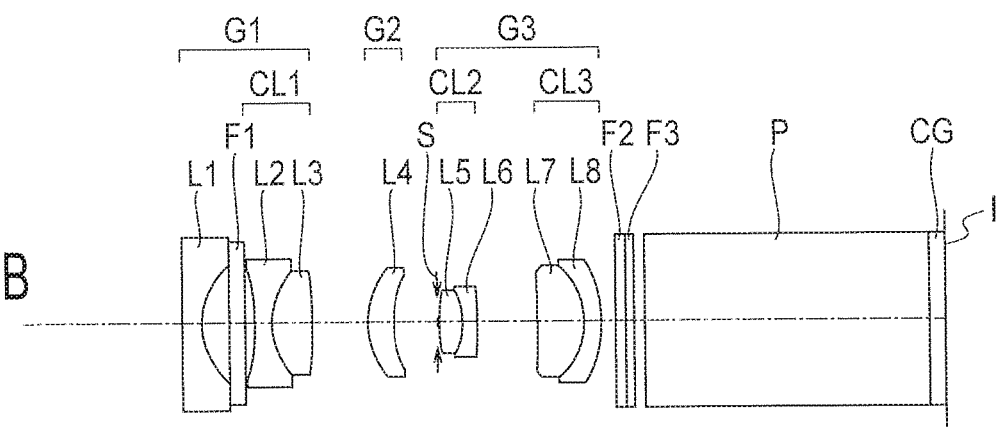
Figure 6A:
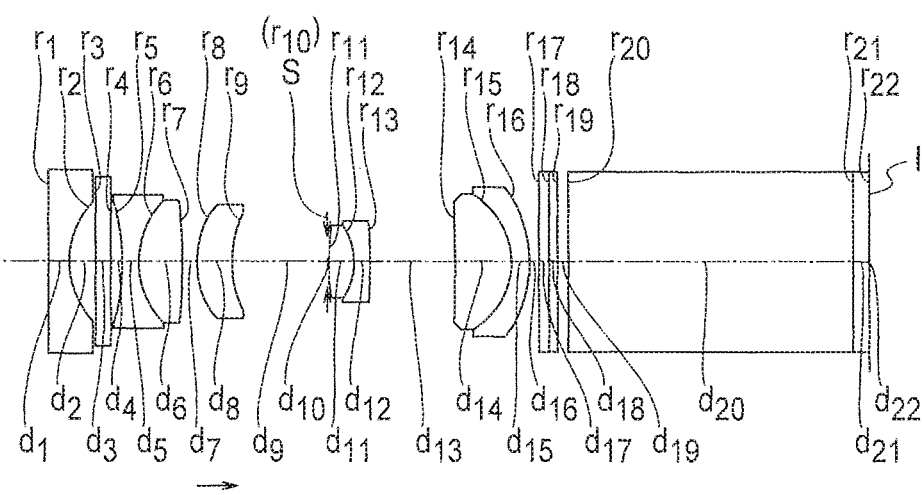
FIG. 6A and FIG. 6B are cross-sectional views of an objective optical system of an example 3.
Figure 6B:
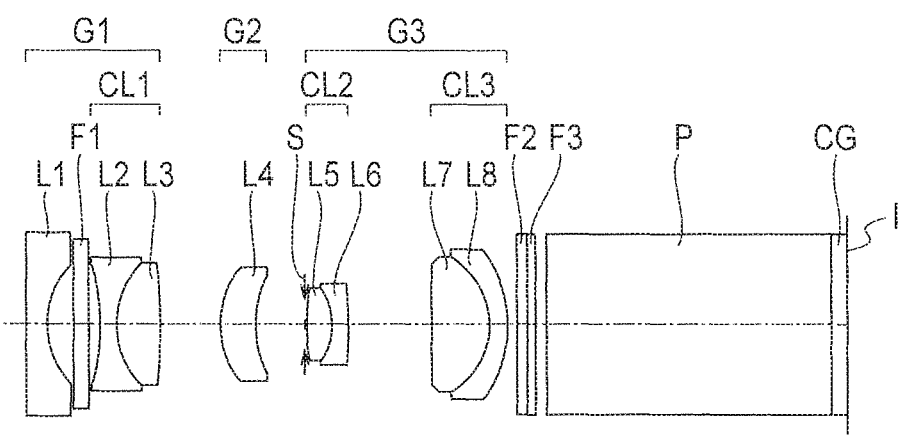
Figure 8A:
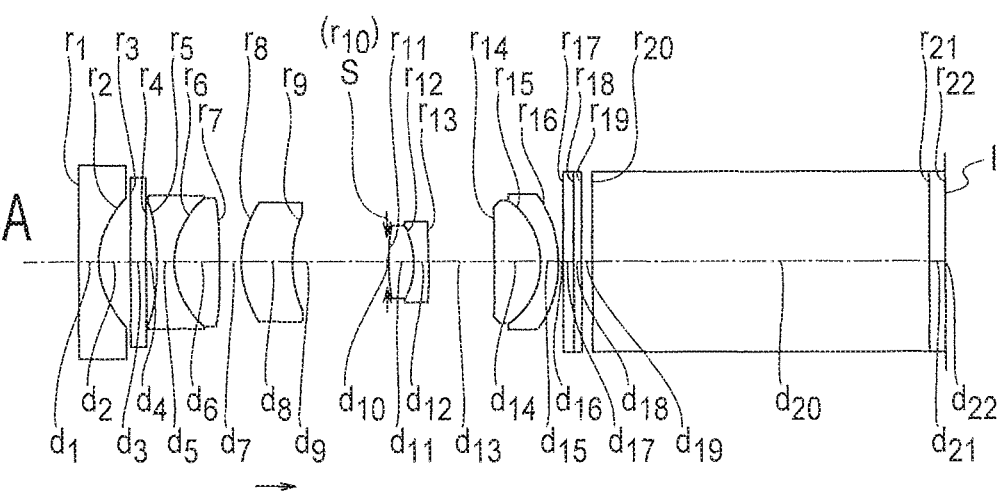
FIG. 8A and FIG. 8B are cross-sectional views of an objective optical system of an example 4.
Figure 8B:
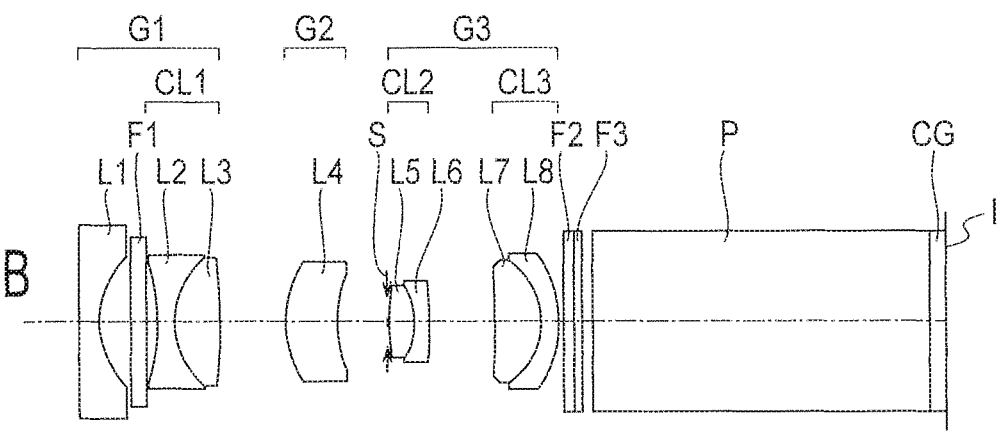
Figure 10A:
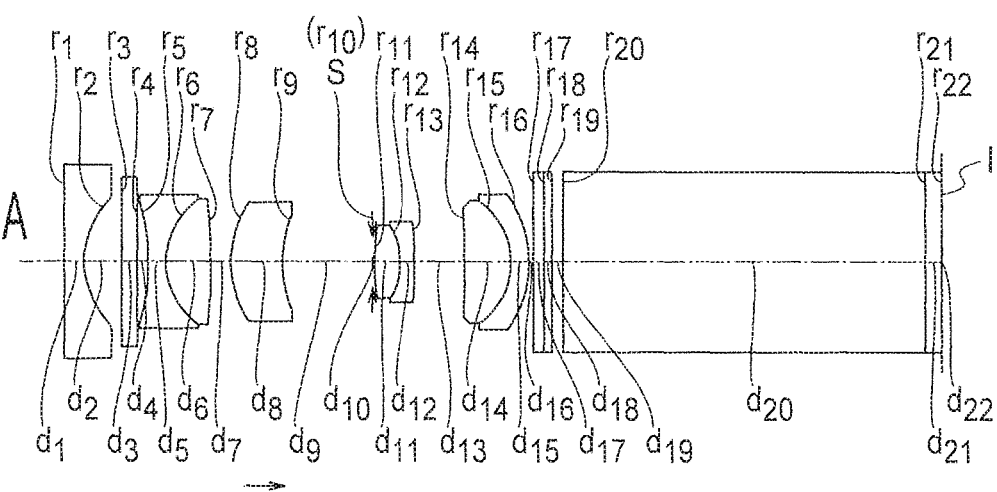
FIG. 10A and FIG. 10B are cross-sectional views of an objective optical system of an example 5.
Figure 10B:
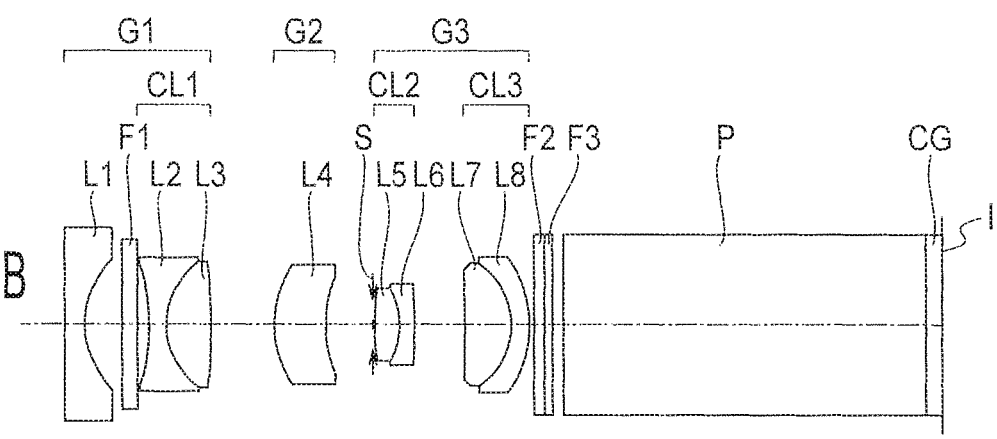
Figure 12A:
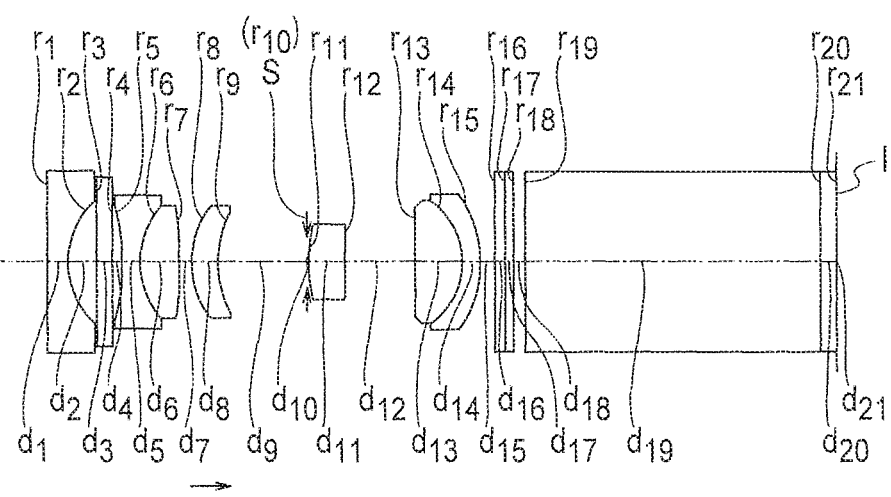
FIG. 12A and FIG. 12B are cross-sectional views of an objective optical system of an example 6.
Figure 12B:
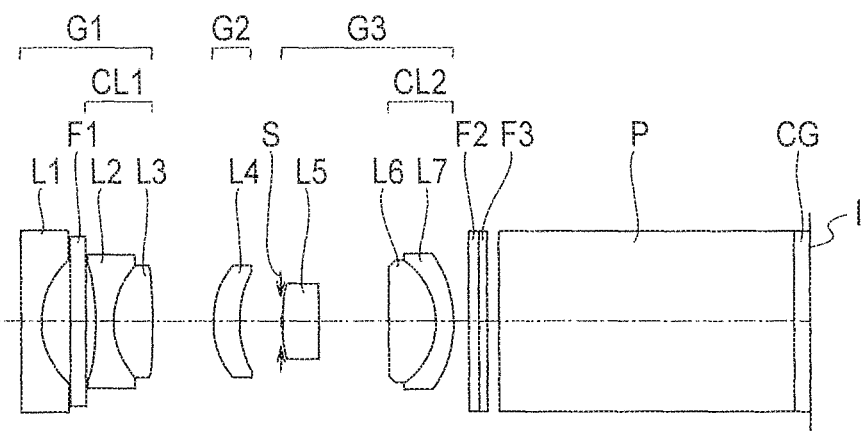
Figure 14A:
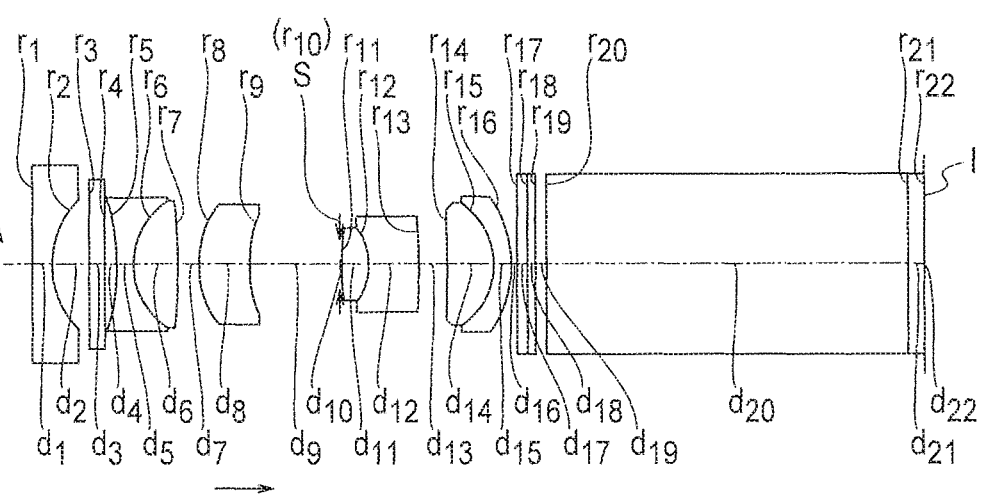
FIG. 14A and FIG. 14B are cross-sectional views of an objective optical system of an example 7.
Figure 14B:
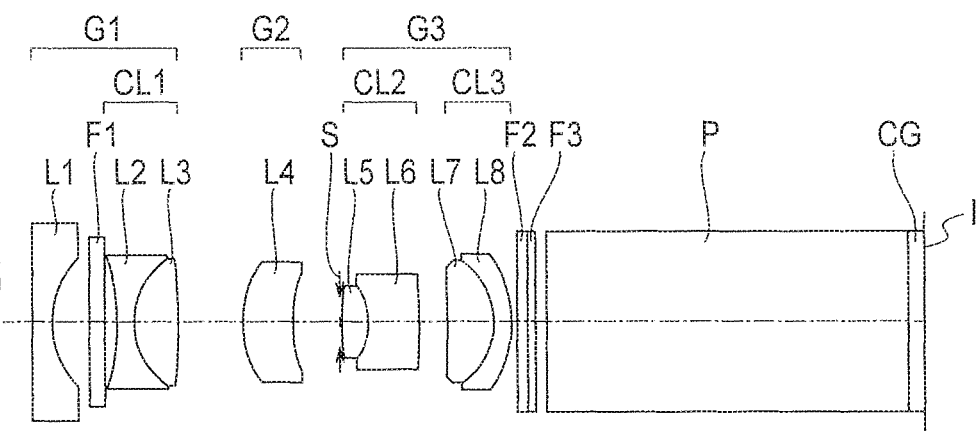
Figure 16A:
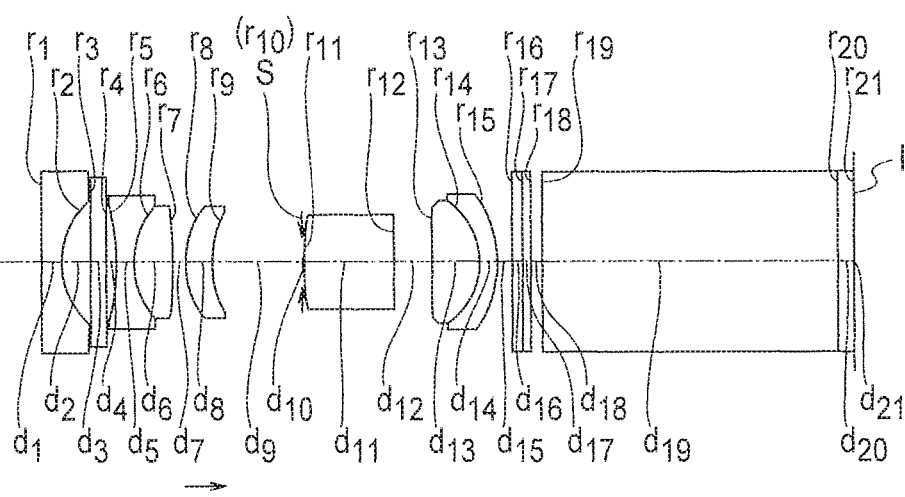
FIG. 16A and FIG. 16B are cross-sectional views of an objective optical system of an example 8.
Figure 16B:
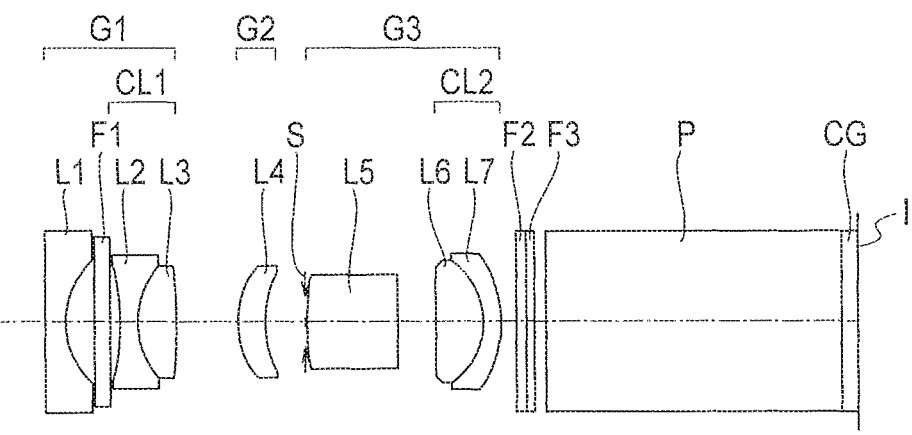

Specific arrangement examples of the basic arrangement will be described below. FIG. 1A, FIG. 1B, and FIG. 1C are cross-sectional views showing specific arrangements of the objective optical system according to the present embodiment. FIG. 1A is a cross-sectional view of an arrangement example 1, FIG. 1B is a cross-sectional view of an arrangement example 2, and FIG. 1C is a cross-sectional view of an arrangement of a prism.

In the arrangement example 1, an objective optical system includes in order from an object side to an image side, a first lens group G1 having a negative refractive power, a second lens group G2 having a positive refractive power, and a third lens group G3 having a positive refractive power. An aperture stop S is disposed between the second lens group G2 and the third lens group G3.

The first lens group G1 includes in order from the object side to the image side, a first lens L1 having a negative refractive power, a second lens L2 having a negative refractive power, and a third lens L3 having a positive refractive power. The second lens L2 and the third lens L3 are cemented, and form a cemented lens CL1.

The second lens group G2 includes a fourth lens L4 having a positive refractive power.

The third lens group G3 includes in order from the object side to the image side, a fifth lens L5 having a positive refractive power, a sixth lens L6 having a negative refractive power, a seventh lens L7 having a positive refractive power, and an eighth lens L8 having a negative refractive power. The firth lens L5 and the sixth lens L6 are cemented, and form a cemented lens CL2. The seventh lens L7 and the eighth lens L8 are cemented, and form a cemented lens CL3.

In the arrangement example 1, focusing is carried out by moving the second lens group G2. FIG. 1A shows a state of having focused to an object at a long distance. In focusing to an object at a short distance, the second lens group G2 moves toward the image side.

A first plane parallel plate F1 is disposed between the first lens L1 and the second lens L2. It is possible to dispose the first plane parallel plate F1 at an arbitrary position in the optical system. A second plane parallel plate F2 and a third plane parallel plate F3 are disposed on the image side of the eighth lens L8. The second plane parallel plate F2 and the third plane parallel plate F3 are cemented.

A prism P is disposed on the image side of the third plane parallel plate F3. A plane parallel plate CG is disposed on the image side of the prism P. The plane parallel plate CG is a cover glass of an image sensor. The image sensor (not shown in the diagram) is disposed on the image side of the plane parallel plate CG. An image-side surface of the plane parallel plate CG is an image plane I. An image pickup surface of the image sensor is aligned with the image-side surface of the plane parallel plate CG.

As shown in FIG. 1C, the prism P is formed by a first prism P1 and a second prism P2. The first prism P1 and the second prism P2 are cemented by a cementing material for example.

A cemented surface is formed by cementing the first prism P1 and the second prism P2. The cemented surface is a polarization beam splitter surface. P-polarized light is reflected at the polarization beam splitter surface and S-polarized light is transmitted through the polarization beam splitter surface. A direction of polarization of the P-polarized light is orthogonal to a direction of polarization of the S-polarized light.

Light emerged from the objective optical system travels along an optical axis AX and is incident on the first prism P1. Out of the light incident on the first prism P1, the P-polarized light is reflected at the cemented surface, and travels along an optical path A. The S-polarized light passes through the cemented surface, and travels along an optical path B. In such manner, two optical paths are formed at the prism P.

The light travelling along the optical path A passes through a ¼ wavelength plate WL, and reaches a reflecting element REF. Light that has reached the reflecting element REF is reflected at a reflecting surface Rs1. The reflected light passes through the ¼ wavelength plate WL, the first prism P1, the cemented surface, the second prism P2, and the plane parallel plate CG, and reaches the image plane I.

The light travelling along the optical path B reaches a reflecting surface Rs2 of the second prism P2. Light that has reached the reflecting surface Rs2 is reflected at the reflecting surface Rs2. The reflected light passes through the second prism P2 and the plane parallel plate CG, and reaches the image plane I.

The image pickup surface of an image sensor IM is positioned at a position of the image plane I. The optical path A and the optical path B are formed in parallel to the image pickup surface. Accordingly, two optical images are formed in parallel on the image pickup surface. Moreover, a length of the optical path A and a length of the optical path B are different. Therefore, two optical images with different focusing positions are formed on the image pickup surface. The two optical images are captured up by the image sensor IM.

In the arrangement example 2, an objective optical system includes in order from an object side to an image side, a first lens group G1 having a negative refractive power, a second lens group G2 having a positive refractive power, and a third lens group G3 having a positive refractive power. An aperture stop S is disposed between the second lens group G2 and the third lens group G3.

The first lens group G1 includes in order from the object side to the image side, a first lens L1 having a negative refractive power, a second lens L2 having a negative refractive power, and a third lens L3 having a positive refractive power. The second lens L2 and the third lens L3 are cemented, and form a cemented lens CL1.

The second lens group G2 includes a fourth lens L4 having a positive refractive power.

The third lens group G3 includes in order from the object side to the image side, a fifth lens L5 having a positive refractive power, a sixth lens L6 having a positive refractive power, and a seventh lens L7 having a negative refractive power. The sixth lens L6 and the seventh lens L7 are cemented, and form a cemented lens CL2.

In the arrangement example 2, focusing is carried out by moving the second lens group G2. FIG. 1B shows a state of having focused to an object at a long distance. In focusing to an object at a short distance, the second lens group G2 moves toward the image side.

In the arrangement example 1 and the arrangement example 2, the aperture stop S is disposed between the second lens group G2 and the third lens group G3. By disposing the aperture stop S at this position, it is possible to lower a height of a light ray passing through the second lens group G2. As a result, it is possible to make small an outer diameter of the second lens group G2.

The second lens group G2 moves at the time of focusing. By the second lens group G2 moving, wherever an object is positioned between a long distance and a short distance, it is possible to carry out focusing. The normal observation is possible when focused to an object at a long distance and the magnifying observation is possible when focused to an object at a short distance.

A moving mechanism is necessary for moving the second lens group G2 in an optical-axial direction. As mentioned above, since it is possible to make the second lens group G2 small-sized, it is easily possible to dispose the moving mechanism around the second lens group G2.

Moreover, the number of lens groups that move being one, it is possible to make the lens group to be moved light-weight. Consequently, it is possible to reduce a load exerted to the moving mechanism. Furthermore, it is possible to simplify the moving mechanism.

An actuator is an example of the moving mechanism. The actuator is to be connected to a lens frame holding the second lens group G2, and accordingly a driving force is imparted to the lens frame.

In the arrangement example 1 and the arrangement example 2, the first plane parallel plate F1 is disposed in the first lens group G1. The first plane parallel plate F1 is an optical filter for cutting off specific wavelengths such as, laser light of YAG laser (light of 1060 nm wavelength), laser light of semiconductor laser (light of 810 nm wavelength), or light of a wavelength of a near infrared region.

The arrangement example 1 and the arrangement example 2, for instance, are objective optical systems having the following specifications.
angle of view: 140° to 165°
back focus: less than four times of a focal length
overall length: less than 12 times of the focal length
F-number: 4.2

In the arrangement example 1, the objective optical system includes eight single lenses. In the arrangement example 2, the objective optical system includes seven single lenses. In such manner, in the arrangement example 1 and the arrangement example 2, since the optical system includes a small number of lenses, it is possible to realize a compact objective optical system.

The objective optical system according to the present embodiment has the abovementioned basic arrangement, and the following conditional expression (1) is satisfied:

$$0.45 < d3t/f32 < 0.8 \quad (1),$$

where,
$d3t$ denotes a distance on an optical axis from a lens surface positioned nearest to an object in the front group up to a lens surface positioned nearest to the object in the rear group, and
$f32$ denotes a focal length of the rear group.

By satisfying conditional expression (1), it is possible to keep the rear group adequately distant from the front group. In this case, it is possible to separate an axial light beam and an off-axis light beam at a position of the rear group. Consequently, it is possible to correct mainly the axial aberration favorably by the front group, and to correct mainly the off-axis aberration favorably by the rear group. As a result, it is possible to maintain a favorable imaging performance with a small number of lenses.

In a case of falling below a lower limit value of conditional expression (1), it is not possible to keep the rear group adequately distant from the front group. Consequently, it is not possible to correct the off-axis aberration favorably by the rear group. In a case of exceeding an upper limit value of conditional expression (1), the rear group is excessively distant from the front group. Consequently, an overall length of the third lens group becomes long, and a lens diameter in the third lens group becomes large.

In the objective optical system according to the present embodiment, it is preferable that the following conditional expression (2) be satisfied:

$$1.2 < f31/f32 < 5.0 \quad (2),$$

where,
$f31$ denotes a focal length of the front group, and
$f32$ denotes the focal length of the rear group.

By satisfying conditional expression (2), it is possible to make the refractive power of the rear group larger than the refractive power of the front group. When the refractive power of the rear group is made large, a principal-point position of the third lens group is positioned on the image side. As a result, it is possible to make the back focus long.

In a case of falling below a lower limit value of conditional expression (2), the refractive power of the front group becomes large. Consequently, the axial aberration is not corrected thoroughly. Moreover, when the refractive power of the front group becomes large, the principal point position of the third lens group is positioned on the object side. Consequently, it is not possible to secure the back focus of an adequate length.

In a case of exceeding an upper limit value of conditional expression (2), the refractive power of the rear group becomes large. Consequently, the off-axis aberration is not corrected thoroughly. Particularly, the coma which occurs in the third lens group becomes small. Consequently, by the coma in the third lens group even together with the coma that occurs in the first lens group, it is not possible to cancel the coma which occurs in the second lens group. Moreover, an overall length of the third lens group becomes long.

It is more preferable that the following conditional expression (2') be satisfied instead of conditional expression (2).

$$1.23 < f31/f32 < 5.0 \quad (2')$$

In the objective optical system according to the present embodiment, it is preferable that the following conditional expression (3) be satisfied:

$$0.28 < d3p/f32 < 0.5 \quad (3),$$

where, d3p denotes a distance on the optical axis from a lens surface positioned nearest to an image in the front group up to the lens surface positioned nearest to an object in the rear group, and f32 denotes the focal length of the rear group.

By satisfying conditional expression (3), it is possible to keep the rear group adequately distant from the front group. In this case, it is possible to separate an axial light beam and an off-axis light beam at the position of the rear group. Consequently, it is possible to correct mainly the axial aberration favorably by the front group, and to correct mainly the off-axis aberration favorably by the rear group. As a result, it is possible to maintain a favorable imaging performance with a small number of lenses.

In a case of falling below a lower limit value of conditional expression (3), it is not possible to keep the rear group adequately distant from the front group. Consequently, it is not possible to correct the off-axis aberration favorably by the rear group. In a case of exceeding an upper limit value of conditional expression (3), the rear group is excessively distant from the front group. Consequently, the overall length of the third lens group becomes long, and the lens diameter in the third lens group becomes large.

It is more preferable that the following conditional expression (3') be satisfied instead of conditional expression (3).

$$0.282 < d3p/f32 < 0.5 \quad (3')$$

It is even more preferable that the following conditional expression (3") be satisfied instead of conditional expression (3).

$$0.295 < d3p/f32 < 0.5 \quad (3'')$$

In the objective optical system according to the present embodiment, it is preferable that the following conditional expression (4) be satisfied:

$$2.3 < f3/f < 3.2 \quad (4),$$

where, f3 denotes a focal length of the third lens group, and
f denotes a focal length of the objective optical system at the time of normal observation.

For securing an adequately long back focus, the refractive power of the third lens group is to be made small or the magnification of the third lens group is to be made large.

In a case of falling below a lower limit value of conditional expression (4), the refractive power of the third lens group becomes large. Consequently, it is not possible to secure an adequate back focus, and moreover, it is not possible to correct an aberration favorably.

In a case of exceeding an upper limit value of conditional expression (4), the overall length of the optical system becomes long, and an outer diameter of the optical system becomes large. Consequently, when the objective optical system is installed in an endoscope, a diameter of an insertion portion becomes large. As a result, an operability of the endoscope is degraded. Moreover, a resistance at the time of inserting inside a body cavity becomes high.

In the objective optical system according to the present embodiment, it is preferable that the first lens group include in order from the object side, a negative lens and a cemented lens, an image-side surface of the negative lens is a surface which is concave toward the image side, an object-side surface of the cemented lens is a surface which is concave toward the object side, the second lens group includes a positive lens, an image-side surface of the positive lens is a surface which is concave toward the image side, and at the time of focusing from an object at a long distance to an object at a short distance, the second lens group moves from the object side toward the image side.

In the first lens group, an object-side negative lens is disposed nearest to an object. It is preferable to make an image-side surface of the object-side negative lens a surface which is concave toward the image side. By doing so, it is possible to correct favorably the coma which occurs in the second lens group, by the first lens group and the third lens group.

Moreover, in the first lens group, an image-side cemented lens is disposed on the image side of the object-side negative lens. It is preferable to make an object-side surface of the image-side cemented lens a surface which is concave toward the object side. By doing so, it is possible to direct a surface in a direction opposite to a direction of a surface which is concentric with the aperture stop. As a result, it is possible to correct the astigmatic difference which occurs in the first lens group. Furthermore, it is possible to correct the chromatic aberration of magnification favorably without making large an outer diameter of an object-side surface of the object-side negative lens.

Moreover, the second lens group includes a positive lens. It is preferable to make an image-side surface of the positive lens a surface which is concave toward the image side. Moreover, at the time of focusing from an object at a long distance to an object at a short distance, the second lens group is to be moved from the object side toward the image side.

When such an arrangement is made, even in a case in which an object position is close to the optical system, it is possible to make small each of an amount of variation in the coma in the first lens group and an amount of variation in the coma in the second lens group while correcting by the second lens group, while the astigmatic difference which occurs in the first lens group is corrected by the second lens group.

Furthermore, not only that it is possible to make small the variation in each coma but also to cancel mutually the coma. As a result, in the optical system as a whole, it is possible to suppress the coma small. Moreover, it is possible to make small the number of lenses to be used in the second lens group.

It is preferable that the aperture stop be disposed between the second lens group and the third lens group. It is more preferable to dispose the aperture stop near a lens positioned nearest to an object in the third lens group.

Example of the objective optical system will be described below in detail by referring to the accompanying diagrams. However, the present disclosure is not restricted to the examples described below.

Lens cross-sectional views of each example will be described below.

FIG. 2A, FIG. 4A, FIG. 6A, FIG. 8A, FIG. 10A, FIG. 12A, FIG. 14A, and FIG. 16A are cross-sectional views in a normal observation state.

FIG. 2B, FIG. 4B, FIG. 6B, FIG. 8B, FIG. 10B, FIG. 12B, FIG. 14B, and FIG. 16B are cross-sectional views in a magnifying observation state.

A first lens group is denoted by G1, a second lens group is denoted by G2, a third lens group is denoted by G3, an aperture stop is denoted by S, a prism is denoted by P, and an image plane (image pickup surface) is denoted by I. A plane parallel plate is denoted by F1, F2, F3, and CG. A plane parallel plate CG is a cover glass and is disposed between the prism P and the image plane I.

The first plane parallel plate F1 is a filter for cutting off specific wavelengths such as, laser light of YAG laser (light of 1060 nm wavelength), laser light of semiconductor laser (light of 810 nm wavelength), or light of a wavelength of a near infrared region. The plane parallel plate F2 and the plane parallel plate F3 are filters having a depolarization effect.

Aberration diagrams of each example will be described below.

FIG. 3A, FIG. 5A, FIG. 7A, FIG. 9A, FIG. 11A, FIG. 13A, FIG. 15A, and FIG. 17A show a spherical aberration (SA) in the normal observation state.

FIG. 3B, FIG. 5B, FIG. 7B, FIG. 9B, FIG. 11B, FIG. 13B, FIG. 15B, and FIG. 17B show an astigmatism (AS) in the normal observation state.

FIG. 3C, FIG. 5C, FIG. 7C, FIG. 9C, FIG. 11C, FIG. 13C, FIG. 15C, and FIG. 17C show a chromatic aberration of magnification (CC) in the normal observation state.

FIG. 3D, FIG. 5D, FIG. 7D, FIG. 9D, FIG. 11D, FIG. 13D, FIG. 15D, and FIG. 17D show a distortion (DT) in the normal observation state.

FIG. 3E, FIG. 5E, FIG. 7E, FIG. 9E, FIG. 11E, FIG. 13E, FIG. 15E, and FIG. 17E show a coma (CM) in the normal observation state.

FIG. 3F, FIG. 5F, FIG. 7F, FIG. 9F, FIG. 11F, FIG. 13F, FIG. 15F, and FIG. 17F show a spherical aberration (SA) in the magnifying observation state.

FIG. 3G, FIG. 5G, FIG. 7G, FIG. 9G, FIG. 11G, FIG. 13G, FIG. 15G, and FIG. 17G show an astigmatism (AS) in the magnifying observation state.

FIG. 3H, FIG. 5H, FIG. 7H, FIG. 9H, FIG. 11H, FIG. 13H, FIG. 15H, and FIG. 17H show a chromatic aberration of magnification (CC) in the magnifying observation state.

FIG. 3I, FIG. 5I, FIG. 7I, FIG. 9I, FIG. 11I, FIG. 13I, FIG. 15I, and FIG. 17I show a distortion (DT) in the magnifying observation state.

FIG. 3J, FIG. 5J, FIG. 7J, FIG. 9J, FIG. 11J, FIG. 13J, FIG. 15J, and FIG. 17J show a coma (CM) in the magnifying observation state.

The coma is indicated by a transverse aberration. An image-height position is a position which is 0.8 times the maximum image height. For example, in a case in which the maximum image height is 1.141 mm, the image-height position becomes 0.913 mm.

In each aberration diagram, a horizontal axis indicates an aberration amount. For the spherical aberration, the astigmatism, the chromatic aberration of magnification, and the coma, the unit of aberration amount is mm. Moreover, for the distortion, the unit of aberration amount is %. Moreover, FNO denotes a F-number, FIY denotes an image height, and the unit thereof is mm (millimeter). Furthermore, the unit of wavelength of an aberration curve is nm.

Example 1

An objective optical system according to an example 1 will be described below. The objective optical system of the example 1 includes in order from an object side to an image side, a first lens group G1 having a negative refractive power, a second lens group G2 having a positive refractive power, and a third lens group G3 having a positive refractive power.

The first lens group G1 includes a planoconcave negative lens L1 of which an object side is a flat surface, a biconcave negative lens L2, and a biconvex positive lens L3. Here, the biconcave negative lens L2 and the biconvex positive lens L3 form a cemented lens CL1.

The second lens group G2 includes a positive meniscus lens L4 having a convex surface directed toward the object side.

The third lens group G3 includes a biconvex positive lens L5, a negative meniscus lens L6 having a convex surface directed toward the image side, a biconvex positive lens L7, and a negative meniscus lens L8 having a convex surface directed toward the image side. Here, the biconvex positive lens L5 and the negative meniscus lens L6 form a cemented lens CL2. The biconvex positive lens L7 and the negative meniscus lens L8 form a cemented lens CL3.

An aperture stop S is disposed between the second lens group G2 and the third lens group G3.

At a time of focusing, the second lens group G2 moves. At the time of focusing from a state of being focused to an object at a long distance to an object at a short distance, the second lens group G2 moves toward the image side.

A plane parallel plate F1 is disposed on the image side of the planoconcave negative lens L1. A plane parallel plate F2, a plane parallel plate F3, a prism P, and a cover glass CG are disposed on the image side of the third lens group G3.

An aspherical surface is provided to an object-side surface of the biconvex positive lens L7.

Example 2

An objective optical system according to an example 2 will be described below. The objective optical system according to the example 2 includes in order from an object side to an image side, a first lens group G1 having a negative refractive power, a second lens group G2 having a positive refractive power, and a third lens group G3 having a positive refractive power.

The first lens group G1 includes a planoconcave negative lens L1 of which an object side is a flat surface, a biconcave negative lens L2, and a biconvex positive lens L3. Here, the biconcave negative lens L2 and the biconvex positive lens L3 form a cemented lens CL1.

The second lens group G2 includes a positive meniscus lens L4 having a convex surface directed toward the object side.

The third lens group G3 includes a biconvex positive lens L5, a negative meniscus lens L6 having a convex surface directed toward the image side, a biconvex positive lens L7, and a negative meniscus lens L8 having a convex surface directed toward the image side. Here, the biconvex positive lens L5 and the negative meniscus lens L6 form a cemented lens CL2. The biconvex positive lens L7 and the negative meniscus lens L8 form a cemented lens CL3.

An aperture stop S is disposed between the second lens group G2 and the third lens group G3.

At a time of focusing, the second lens group G2 moves. At the time of focusing from a state of being focused to an object at a long distance to an object at a short distance, the second lens group G2 moves toward the image side.

A plane parallel plate F1 is disposed on the image side of the planoconcave negative lens L1. A plane parallel plate F2, a plane parallel plate F3, a prism P, and a cover glass CG are disposed on the image side of the third lens group G3.

An aspherical surface is provided to an object-side surface of the biconvex positive lens L7.

Example 3

An objective optical system according to an example 3 will be described below. The objective optical system according to the example 3 includes in order from an object side to an image side, a first lens group G1 having a negative refractive power, a second lens group G2 having a positive refractive power, and a third lens group G3 having a positive refractive power.

The first lens group G1 includes a planoconcave negative lens L1 of which an object side is a flat surface, a biconcave negative lens L2, and a biconvex positive lens L3. Here, the biconcave negative lens L2 and the biconvex positive lens L3 form a cemented lens CL1.

The second lens group G2 includes a positive meniscus lens L4 having a convex surface directed toward the object side.

The third lens group G3 includes a biconvex positive lens L5, a negative meniscus lens L6 having a convex surface directed toward the image side, a positive meniscus lens L7 having a convex surface directed toward the image side, and a negative meniscus lens L8 having a convex surface directed toward the image side. Here, the biconvex positive lens L5 and the negative meniscus lens L6 form a cemented lens CL2. The positive meniscus lens L7 and the negative meniscus lens L8 form a cemented lens CL3.

An aperture stop S is disposed between the second lens group G2 and the third lens group G3.

At a time of focusing, the second lens group G2 moves. At the time of focusing from a state of being focused to an object at a long distance to an object at a short distance, the second lens group G2 moves toward the image side.

A plane parallel plate F1 is disposed on the image side of the planoconcave negative lens L1. A plane parallel plate F2, a plane parallel plate F3, a prism P, and a cover glass CG are disposed on the image side of the third lens group G3.

An aspherical surface is provided to an object-side surface of the positive meniscus lens L7.

Example 4

An objective optical system according to an example 4 will be described below. The objective optical system according to the example 4 includes in order from an object side to an image side, a first lens group G1 having a negative refractive power, a second lens group G2 having a positive refractive power, and a third lens group G3 having a positive refractive power.

The first lens group G1 includes a planoconcave negative lens L1 of which an object side is a flat surface, a biconcave negative lens L2, and a biconvex positive lens L3. Here, the biconcave negative lens L2 and the biconvex positive lens L3 form a cemented lens CL1.

The second lens group G2 includes a positive meniscus lens L4 having a convex surface directed toward the object side.

The third lens group G3 includes a biconvex positive lens L5, a negative meniscus lens L6 having a convex surface directed toward the image side, a positive meniscus lens L7 having a convex surface directed toward the image side, and a negative meniscus lens L8 having a convex surface directed toward the image side. Here, the biconvex positive lens L5 and the negative meniscus lens L6 form a cemented lens CL2. The positive meniscus lens L7 and the negative meniscus lens L8 form a cemented lens CL3.

An aperture stop S is disposed between the second lens group G2 and the third lens group G3.

At a time of focusing, the second lens group G2 moves. At the time of focusing from a state of being focused to an object at a long distant to an object at a short distance, the second lens group G2 moves toward the image side.

A plane parallel plate F1 is disposed on the image side of the planoconcave negative lens L1. A plane parallel plate F2, a plane parallel plate F3, a prism P, and a cover glass CG are disposed on the image side of the third lens group G3.

An aspherical surface is provided to an object-side surface of the positive meniscus lens L7.

Example 5

An objective optical system according to an example 5 will be described below. The objective optical system according to the example 5 includes in order from an object side to an image side, a first lens group G1 having a negative refractive power, a second lens group G2 having a positive refractive power, and a third lens group G3 having a positive refractive power.

The first lens group G1 includes a planoconcave negative lens L1 of which an object side is a flat surface, a biconcave negative lens L2, and a biconvex positive lens L3. Here, the biconcave negative lens L2 and the biconvex positive lens L3 form a cemented lens CL1.

The second lens group G2 includes a positive meniscus lens L4 having a convex surface directed toward the object side.

The third lens group G3 includes a biconvex positive lens L5, a negative meniscus lens L6 having a convex surface directed toward the image side, a positive meniscus lens L7 having a convex surface directed toward the image side, and a negative meniscus lens L8 having a convex surface directed toward the image side. Here, the biconvex positive lens L5 and the negative meniscus lens L6 form a cemented lens CL2. The positive meniscus lens L7 and the negative meniscus lens L8 form a cemented lens CL3.

An aperture stop S is disposed between the second lens group G2 and the third lens group G3.

At a time of focusing, the second lens group G2 moves. At the time of focusing from a state of being focused to an object at a long distance to an object at a short distance, the second lens group G2 moves toward the image side.

A plane parallel plate F1 is disposed on the image side of the planoconcave negative lens L1. A plane parallel plate F2, a plane parallel plate F3, a prism P, and a cover glass CG are disposed on the image side of the third lens group G3.

An aspherical surface is provided to an object-side surface of the positive meniscus lens L7.

Example 6

An objective optical system according to an example 6 will be described below. The objective optical system according to the example 6 includes in order from an object side to an image side, a first lens group G1 having a negative refractive power, a second lens group G2 having a positive refractive power, and a third lens group G3 having a positive refractive power.

The first lens group G1 includes a planoconcave negative lens L1 of which an object side is a flat surface, a biconcave negative lens L2, and a biconvex positive lens L3. Here, the biconcave negative lens L2 and the biconvex positive lens L3 form a cemented lens CL1.

The second lens group G2 includes a positive meniscus lens L4 having a convex surface directed toward the object side.

The third lens group G3 includes a biconvex positive lens L5, a biconvex positive lens L6, and a negative meniscus lens L7 having a convex surface directed toward the image side. Here, the biconvex positive lens L6 and the negative meniscus lens L7 form a cemented lens CL2.

An aperture stop S is disposed between the second lens group G2 and the third lens group G3.

At a time of focusing, the second lens group G2 moves. At the time of focusing from a state of being focused to an object at a long distance to an object at a short distance, the second lens group G2 moves toward the image side.

A plane parallel plate F1 is disposed on the image side of the planoconcave negative lens L1. A plane parallel plate F2, a plane parallel plate F3, a prism P, and a cover glass CG are disposed on the image side of the third lens group G3.

An aspherical surface is provided to an object-side surface of the biconvex positive lens L5 and an object-side surface of the biconvex positive lens L6.

Example 7

An objective optical system according to an example 7 will be described below. The objective optical system according to the example 7 includes in order from an object side to an image side, a first lens group G1 having a negative refractive power, a second lens group G2 having a positive refractive power, and a third lens group G3 having a positive refractive power.

The first lens group G1 includes a planoconcave negative lens L1 of which an object side is a flat surface, a biconcave negative lens L2, and a biconvex positive lens L3. Here, the biconcave negative lens L2 and the biconvex positive lens L3 form a cemented lens CL1.

The second lens group G2 includes a positive meniscus lens L4 having a convex surface directed toward the object side.

The third lens group G3 includes a biconvex positive lens L5, a negative meniscus lens L6 having a convex surface directed toward the image side, a positive meniscus lens L7 having a convex surface directed toward the image side, and a negative meniscus lens L8 having a convex surface directed toward the image side. Here, the biconvex positive lens L5 and the negative meniscus lens L6 form a cemented surface CL2. The positive meniscus lens L7 and the negative meniscus lens L8 form a cemented surface CL3.

An aperture stop S is disposed between the second lens group G2 and the third lens group G3.

At a time of focusing, the second lens group G2 moves. At the time of focusing from a state of being focused to an object at a long distance to an object at a short distance, the second lens group G2 moves toward the image side.

A plane parallel plate F1 is disposed on the image side of the planoconcave negative lens L1. A plane parallel plate F2, a plane parallel plate F3, a prism P, and a cover glass CG are disposed on the image side of the third lens group G3.

An aspherical surface is provided to an object-side surface of the positive meniscus lens L7.

Example 8

An objective optical system according to an example 8 will be described below. The objective optical system according to the example 8 includes in order from an object side to an image side, a first lens group G1 having a negative refractive power, a second lens group G2 having a positive refractive power, and a third lens group G3 having a positive refractive power.

The first lens group G1 includes a planoconcave negative lens L1 of which an object side is a flat surface, a biconcave negative lens L2, and a biconvex positive lens L3. Here, the biconcave negative lens L2 and the biconvex positive lens L3 form a cemented lens CL1.

The second lens group G2 includes a positive meniscus lens L4 having a convex surface directed toward the object side.

The third lens group G3 includes a biconvex positive lens L5, a biconvex positive lens L6, and a negative meniscus lens L7 having a convex surface directed toward the image side. Here, the biconvex positive lens L6 and the negative meniscus lens L7 form a cemented lens CL2.

An aperture stop S is disposed between the second lens group G2 and the third lens group G3.

At a time of focusing, the second lens group G2 moves. At the time of focusing from a state of being focused to an object at a long distance to an object at a short distance, the second lens group G2 moves toward the image side.

A plane parallel plate F1 is disposed on the image side of the planoconcave negative lens L1. A plane parallel plate F2, a plane parallel plate F3, a prism P, and a cover glass CG are disposed on the image side of the third lens group G3.

An aspherical surface is provided to an object-side surface of the biconvex positive lens L5 and an object-side surface of the biconvex positive lens L6.

Numerical data of each example described above is shown below. In surface data, r denotes radius of curvature of each lens surface, d denotes a distance between respective lens surfaces, ne denotes a refractive index of each lens for a e-line, vd denotes an Abbe number for each lens, and * denotes an aspherical surface. Stop denotes an aperture stop.

In Various data, OBJ denotes an object distance, f denotes a focal length for e-line, Fno denotes an F number, ω denotes a half angle of view, and IH denotes an image height. Each of the focal length and the F number is a focal length of the normal observation and a F number of the normal observation. In a close observation state, it is possible to carry out the magnifying observation.

A shape of an aspherical surface is defined by the following expression where the direction of the optical axis is represented by z, the direction orthogonal to the optical axis is represented by y, a conical coefficient is represented by k, aspherical surface coefficients are represented by A4, A6, A8, A10, A12 . . . .

$$Z=(y^2/r)/[1+\{1-(1+k)(y/r)^2\}^{1/2}]+A4y^4+A6y^6+A8y^8+A10y^{10}+A12y^{12}+\ldots$$

Further, in the aspherical surface coefficients, 'e-n' (where, n is an integral number) indicates '10$^{-n}$'.

Example 1

Unit mm

Surface data

| Surface no. | r | d | ne | vd |
|---|---|---|---|---|
| 1 | ∞ | 0.4000 | 1.88815 | 40.76 |
| 2 | 1.6173 | 0.6234 | 1. | |
| 3 | ∞ | 0.3000 | 1.52300 | 65.12 |
| 4 | ∞ | 0.2296 | 1. | |
| 5 | -3.8077 | 0.3200 | 1.88815 | 40.76 |
| 6 | 1.6097 | 0.8710 | 1.85504 | 23.78 |
| 7 | -8.9002 | d7 | 1. | |
| 8 | 1.6874 | 0.5682 | 1.48915 | 70.23 |
| 9 | 2.0105 | d9 | 1. | |
| 10(Stop) | ∞ | 0.0300 | 1. | |
| 11 | 3.5510 | 0.4500 | 1.68084 | 54.89 |
| 12 | -1.3567 | 0.3000 | 1.82017 | 46.62 |
| 13 | -12.9458 | 1.2362 | 1. | |
| 14* | 92.3170 | 0.9000 | 1.68084 | 54.89 |
| 15 | -1.4523 | 0.3500 | 1.85504 | 23.78 |
| 16 | -2.3536 | 0.2964 | 1. | |
| 17 | ∞ | 0.2000 | 1.54617 | 69.87 |
| 18 | ∞ | 0.1600 | 1.37860 | 106.18 |
| 19 | ∞ | 0.2200 | 1. | |
| 20 | ∞ | 5.5410 | 1.64129 | 55.38 |
| 21 | ∞ | 0.3199 | 1.50700 | 63.26 |
| 22 | ∞ | 0. | 1. | |
| Imaging surface | ∞ | | | |

Aspherical surface data

14th surface k = -34.9348
A4 = -1.6411e-02, A6 = 1.8958e-03, A8 = -5.5499e-04

Various data

| | Normal observation state | Close observation state |
|---|---|---|
| OBJ | 18.00000 | 3.55000 |
| f | 1.107 | |
| Fno | 4.19 | |
| ω | 79.6 | |
| IH | 1.141 | |
| d7 | 0.34590 | 1.19161 |
| d9 | 1.81407 | 0.96836 |

Example 2

Unit mm

Surface data

| Surface no. | r | d | ne | vd |
|---|---|---|---|---|
| 1 | ∞ | 0.4000 | 1.88815 | 40.76 |
| 2 | 1.4893 | 0.5300 | 1. | |
| 3 | ∞ | 0.3000 | 1.52300 | 65.12 |
| 4 | ∞ | 0.1992 | 1. | |
| 5 | -3.3750 | 0.3200 | 1.88815 | 40.76 |
| 6 | 1.4969 | 0.8016 | 1.85504 | 23.78 |
| 7 | -9.6452 | d7 | 1. | |
| 8 | 1.6129 | 0.5058 | 1.48915 | 70.23 |
| 9 | 1.8991 | d9 | 1. | |
| 10(Stop) | ∞ | 0.0192 | 1. | |
| 11 | 2.8602 | 0.4500 | 1.65141 | 53.02 |
| 12 | -1.4550 | 0.3000 | 1.82017 | 46.62 |
| 13 | -9.6340 | 1.1665 | 1. | |
| 14* | 686.1721 | 0.9000 | 1.68084 | 54.89 |
| 15 | -1.3926 | 0.3500 | 1.85504 | 23.78 |
| 16 | -2.3789 | 0.2646 | 1. | |
| 17 | ∞ | 0.2000 | 1.54617 | 69.87 |
| 18 | ∞ | 0.1600 | 1.37860 | 106.18 |
| 19 | ∞ | 0.2200 | 1. | |
| 20 | ∞ | 5.5410 | 1.64129 | 55.38 |
| 21 | ∞ | 0.3179 | 1.50700 | 63.26 |
| 22 | ∞ | 0. | 1. | |
| Imaging surface | ∞ | | | |

Aspherical surface data

14th surface k = 363.9601
A4 = -1.7143e-02, A6 = -2.7983e-04, A8 = 6.2807e-04

Various data

| | Normal observation state | Close observation state |
|---|---|---|
| OBJ | 18.00000 | 3.55000 |
| f | 1.101 | |
| Fno | 4.25 | |
| ω | 80.5 | |
| IH | 1.141 | |
| d7 | 0.27139 | 1.07873 |
| d9 | 1.68431 | 0.87697 |

Example 3

Unit mm

Surface data

| Surface no. | r | d | ne | vd |
|---|---|---|---|---|
| 1 | ∞ | 0.4000 | 1.88815 | 40.76 |
| 2 | 1.6216 | 0.5194 | 1. | |
| 3 | ∞ | 0.3000 | 1.52300 | 65.12 |
| 4 | ∞ | 0.2296 | 1. | |
| 5 | -3.8454 | 0.3200 | 1.88815 | 40.76 |
| 6 | 1.7180 | 0.8710 | 1.85504 | 23.78 |
| 7 | -8.8093 | d7 | 1. | |
| 8 | 1.8043 | 0.6868 | 1.48915 | 70.23 |
| 9 | 2.2380 | d9 | 1. | |
| 10 (Stop) | ∞ | 0.0300 | 1. | |
| 11 | 4.1205 | 0.5200 | 1.68084 | 54.89 |
| 12 | -1.2815 | 0.3000 | 1.79196 | 47.37 |
| 13 | -7.8787 | 1.6625 | 1. | |
| 14* | -306.9738 | 1.1000 | 1.68084 | 54.89 |
| 15 | -1.4965 | 0.3500 | 1.85504 | 23.78 |
| 16 | -2.4287 | 0.1692 | 1. | |
| 17 | ∞ | 0.2000 | 1.54617 | 69.87 |
| 18 | ∞ | 0.1600 | 1.37860 | 106.18 |
| 19 | ∞ | 0.2200 | 1. | |
| 20 | ∞ | 5.5410 | 1.64129 | 55.38 |
| 21 | ∞ | 0.3199 | 1.50700 | 63.26 |
| 22 | ∞ | 0. | 1. | |
| Imaging surface | ∞ | | | |

Aspherical surface data

14th surface k = 129.6954
A4 = -1.3827e-02, A6 = 3.0751e-04, A8 = 1.4007e-04

Various data

| | Normal observation state | Close observation state |
|---|---|---|
| OBJ | 18.00000 | 3.55000 |
| f | 1.151 | |

-continued

| Unit mm | | | |
|---|---|---|---|
| Fno | 4.21 | | |
| ω | 70.5 | | |
| IH | 1.141 | | |
| d7 | 0.26875 | 1.12824 | |
| d9 | 1.84054 | 0.98105 | |

Example 4

| Unit mm | | | | |
|---|---|---|---|---|
| Surface data | | | | |
| Surface no. | r | d | ne | vd |
| 1 | ∞ | 0.4000 | 1.88815 | 40.76 |
| 2 | 1.7670 | 0.6201 | 1. | |
| 3 | ∞ | 0.3000 | 1.52300 | 65.12 |
| 4 | ∞ | 0.2296 | 1. | |
| 5 | −3.8611 | 0.3200 | 1.88815 | 40.76 |
| 6 | 1.5941 | 0.8710 | 1.85504 | 23.78 |
| 7 | −9.6188 | d7 | 1. | |
| 8 | 2.0496 | 1.0018 | 1.48915 | 70.23 |
| 9 | 2.6514 | d9 | 1. | |
| 10(Stop) | ∞ | 0.0300 | 1. | |
| 11 | 4.5635 | 0.5200 | 1.68084 | 54.89 |
| 12 | −1.2808 | 0.3000 | 1.79196 | 47.37 |
| 13 | −11.8873 | 1.2686 | 1. | |
| 14* | −69.4642 | 0.9000 | 1.68084 | 54.89 |
| 15 | −1.4727 | 0.3500 | 1.85504 | 23.78 |
| 16 | −2.3227 | 0.1100 | 1. | |
| 17 | ∞ | 0.2000 | 1.54617 | 69.87 |
| 18 | ∞ | 0.1600 | 1.37860 | 106.18 |
| 19 | ∞ | 0.2200 | 1. | |
| 20 | ∞ | 6.5410 | 1.64129 | 55.38 |
| 21 | ∞ | 0.3198 | 1.50700 | 63.26 |
| 22 | ∞ | 0. | 1. | |
| Imaging surface | ∞ | | | |

Aspherical surface data

14th surface k = 303.7869
A4 = −1.3218e−02, A6 = 2.5417e−05, A8 = 2.5201e−04

| Various data | | |
|---|---|---|
| | Normal observation state | Close observation state |
| OBJ | 18.00000 | 3.55000 |
| f | 1.173 | |
| Fno | 4.37 | |
| ω | 69.6 | |
| IH | 1.141 | |
| d7 | 0.43375 | 1.29224 |
| d9 | 1.80847 | 0.94998 |

Example 5

| Unit mm | | | | |
|---|---|---|---|---|
| Surface data | | | | |
| Surface no. | r | d | ne | vd |
| 1 | ∞ | 0.4000 | 1.88815 | 40.76 |
| 2 | 1.8017 | 0.7306 | 1. | |
| 3 | ∞ | 0.3000 | 1.52300 | 65.12 |

-continued

| Unit mm | | | | |
|---|---|---|---|---|
| 4 | ∞ | 0.2296 | 1. | |
| 5 | −4.0155 | 0.3200 | 1.88815 | 40.76 |
| 6 | 1.4687 | 0.8710 | 1.85504 | 23.78 |
| 7 | −10.0338 | d7 | 1. | |
| 8 | 2.0337 | 0.9780 | 1.48915 | 70.23 |
| 9 | 2.6032 | d9 | 1. | |
| 10(Stop) | ∞ | 0.0300 | 1. | |
| 11 | 5.7412 | 0.5200 | 1.68084 | 54.89 |
| 12 | −1.1934 | 0.3000 | 1.79196 | 47.37 |
| 13 | −11.9828 | 0.9523 | 1. | |
| 14* | −61.4190 | 0.9000 | 1.68084 | 54.89 |
| 15 | −1.4242 | 0.3500 | 1.85504 | 23.78 |
| 16 | −2.1999 | 0.1100 | 1. | |
| 17 | ∞ | 0.2000 | 1.54617 | 69.87 |
| 18 | ∞ | 0.1600 | 1.37860 | 106.18 |
| 19 | ∞ | 0.2200 | 1. | |
| 20 | ∞ | 7.0410 | 1.64129 | 55.38 |
| 21 | ∞ | 0.3199 | 1.50700 | 63.26 |
| 22 | ∞ | 0. | 1. | |
| Imaging surface | ∞ | | | |

Aspherical surface data

14th surface k = 237.0071
A4 = −1.5143e−02, A6 = 1.2981e−03, A8 = −3.8382e−04

| Various data | | |
|---|---|---|
| | Normal observation state | Close observation state |
| OBJ | 18.00000 | 3.55000 |
| f | 1.182 | |
| Fno | 4.38 | |
| ω | 69.5 | |
| IH | 1.141 | |
| d7 | 0.40910 | 1.27441 |
| d9 | 1.77117 | 0.90586 |

Example 6

| Unit mm | | | | |
|---|---|---|---|---|
| Surface data | | | | |
| Surface no. | r | d | ne | vd |
| 1 | ∞ | 0.4000 | 1.88815 | 40.76 |
| 2 | 1.5105 | 0.5300 | 1. | |
| 3 | ∞ | 0.3000 | 1.52300 | 65.12 |
| 4 | ∞ | 0.1992 | 1. | |
| 5 | −3.7804 | 0.3200 | 1.88815 | 40.76 |
| 6 | 1.5243 | 0.7221 | 1.85504 | 23.78 |
| 7 | −8.7864 | d7 | 1. | |
| 8 | 1.6660 | 0.5194 | 1.48915 | 70.23 |
| 9 | 1.9734 | d9 | 1. | |
| 10(Stop) | ∞ | 0.0283 | 1. | |
| 11* | 3.8348 | 0.6882 | 1.59732 | 67.74 |
| 12 | −52.3813 | 1.3034 | 1. | |
| 13* | 47.4038 | 0.9000 | 1.68084 | 54.89 |
| 14 | −1.3706 | 0.3500 | 1.86784 | 22.73 |
| 15 | −2.2661 | 0.2402 | 1. | |
| 16 | ∞ | 0.2000 | 1.54617 | 69.87 |
| 17 | ∞ | 0.1600 | 1.37860 | 106.18 |
| 18 | ∞ | 0.2200 | 1. | |
| 19 | ∞ | 5.5410 | 1.64129 | 55.38 |
| 20 | ∞ | 0.3171 | 1.50700 | 63.26 |
| 21 | ∞ | 0. | 1. | |
| Imaging surface | ∞ | | | |

Aspherical surface data

-continued

Unit mm

11th surface k = −5.9414

13th surface k = 341.6896
A4 = −1.4297e−02, A6 = 7.3030e−04, A8 = 7.3026e−04

Various data

|  | Normal observation state | Close observation state |
|---|---|---|
| OBJ | 18.00000 | 3.55000 |
| f | 1.105 | |
| Fno | 4.00 | |
| ω | 79.9 | |
| IH | 1.141 | |
| d7 | 0.24059 | 1.14374 |
| d9 | 1.67063 | 0.76748 |

Example 7

Unit mm

Surface data

| Surface no. | r | d | ne | νd |
|---|---|---|---|---|
| 1 | ∞ | 0.4000 | 1.88815 | 40.76 |
| 2 | 1.8159 | 0.7286 | 1. | |
| 3 | ∞ | 0.3000 | 1.52300 | 65.12 |
| 4 | ∞ | 0.2296 | 1. | |
| 5 | −4.0271 | 0.3200 | 1.88815 | 40.76 |
| 6 | 1.4650 | 0.8710 | 1.85504 | 23.78 |
| 7 | −10.1555 | d7 | 1. | |
| 8 | 2.0287 | 0.9794 | 1.48915 | 70.23 |
| 9 | 2.6203 | d9 | 1. | |
| 10(Stop) | ∞ | 0.0300 | 1. | |
| 11 | 5.4027 | 0.5200 | 1.68084 | 54.89 |
| 12 | −1.1831 | 1.0000 | 1.79196 | 47.37 |
| 13 | −13.0433 | 0.5564 | 1. | |
| 14* | −43.7129 | 0.9000 | 1.68084 | 54.89 |
| 15 | −1.4349 | 0.3500 | 1.85504 | 23.78 |
| 16 | −2.2096 | 0.1100 | 1. | |
| 17 | ∞ | 0.2000 | 1.54617 | 69.87 |
| 18 | ∞ | 0.1600 | 1.37860 | 106.18 |
| 19 | ∞ | 0.2200 | 1. | |
| 20 | ∞ | 7.0410 | 1.64129 | 55.38 |
| 21 | ∞ | 0.3194 | 1.50700 | 63.26 |
| 22 | ∞ | 0. | 1. | |
| Imaging surface | ∞ | | | |

Aspherical surface data

14th surface k = 237.0218
A4 = −1.4900e−02, A6 = 1.4311e−03, A8 = −6.0966e−04

Various data

|  | Normal observation state | Close observation state |
|---|---|---|
| OBJ | 18.00000 | 3.55000 |
| f | 1.174 | |
| Fno | 4.32 | |
| ω | 70.5 | |
| IH | 1.141 | |
| d7 | 0.40945 | 1.25505 |
| d9 | 1.76814 | 0.92254 |

Example 8

Unit mm

Surface data

| Surface no. | r | d | ne | νd |
|---|---|---|---|---|
| 1 | ∞ | 0.4000 | 1.88815 | 40.76 |
| 2 | 1.5115 | 0.5300 | 1. | |
| 3 | ∞ | 0.3000 | 1.52300 | 65.12 |
| 4 | ∞ | 0.1992 | 1. | |
| 5 | −3.7868 | 0.3200 | 1.88815 | 40.76 |
| 6 | 1.5255 | 0.7215 | 1.85504 | 23.78 |
| 7 | −8.7499 | d7 | 1. | |
| 8 | 1.6645 | 0.5189 | 1.48915 | 70.23 |
| 9 | 1.9756 | d9 | 1. | |
| 10(Stop) | ∞ | 0.0278 | 1. | |
| 11* | 3.8113 | 1.6993 | 1.59732 | 67.74 |
| 12 | −54.3575 | 0.7091 | 1. | |
| 13* | 48.7589 | 0.9000 | 1.68084 | 54.89 |
| 14 | −1.3696 | 0.3500 | 1.86784 | 22.73 |
| 15 | −2.2689 | 0.2402 | 1. | |
| 16 | ∞ | 0.2000 | 1.54617 | 69.87 |
| 17 | ∞ | 0.1600 | 1.37860 | 106.18 |
| 18 | ∞ | 0.2200 | 1. | |
| 19 | ∞ | 5.5410 | 1.64129 | 55.38 |
| 20 | ∞ | 0.3099 | 1.50700 | 63.26 |
| 21 | ∞ | 0. | 1. | |
| Imaging surface | ∞ | | | |

Aspherical surface data

11th surface k = −5.8413

13th surface k = 341.6894
A4 = −1.4541e−02, A6 = 8.1408e−04, A8 = 9.0620e−04

Various data

|  | Normal observation state | Close observation state |
|---|---|---|
| OBJ | 18.00000 | 3.55000 |
| f | 1.101 | |
| Fno | 3.97 | |
| ω | 80.7 | |
| IH | 1.141 | |
| d7 | 0.24009 | 1.13672 |
| d9 | 1.66916 | 0.77253 |

Next, the values of conditional expressions in each example are shown below.

| | Example1 | Example2 | Example3 | Example4 |
|---|---|---|---|---|
| (1)d3t/f32 | 0.511 | 0.467 | 0.600 | 0.523 |
| (2)f31/f32 | 1.678 | 1.236 | 1.366 | 1.937 |
| (3)d3p/f32 | 0.318 | 0.284 | 0.402 | 0.318 |
| (4)f3/f | 2.879 | 2.786 | 2.977 | 2.867 |

| | Example5 | Example6 | Example7 | Example8 |
|---|---|---|---|---|
| (1)d3t/f32 | 0.473 | 0.533 | 0.545 | 0.643 |
| (2)f31/f32 | 2.891 | 1.609 | 2.823 | 1.608 |
| (3)d3p/f32 | 0.254 | 0.349 | 0.146 | 0.189 |
| (4)f3/f | 2.782 | 2.799 | 2.785 | 2.818 |

Various embodiments of the present disclosure are described above. However, the present disclosure is not restricted to these embodiments, and embodiments formed by combining arrangement of these embodiments without departing from the scope of the present disclosure are also included in the category of the present disclosure.

(Note)

A disclosure of the following arrangement is derived from the examples described above.

(Appended Mode)

In the objective optical system, the first lens group includes from the object side, a negative lens and a cemented lens, an image-side surface of the negative lens is a surface which is concave toward the image side, an object-side surface of the cemented lens is a surface which is concave toward the object side, the second lens group includes a positive lens, an image-side surface of the positive lens is a surface which is concave toward the image side, and at the time of focusing from an object at a long distance to an object at a short distance, the second lens group moves from the object side toward the image side.

According to the present disclosure, it is possible to provide an objective optical system in which the overall length is short while having an adequate back focus, and various aberrations are corrected favorably, and an endoscope.

The present disclosure is useful for an objective optical system in which the overall length is short while having an adequate back focus, and various aberrations are corrected favorably, and for an endoscope.

What is claimed is:

1. An objective optical system comprising in order from an object side to an image side:
a first lens group having a negative refractive power;
a second lens group; and
a third lens group having a positive refractive power,
wherein:
at a time of focusing, the second lens group moves in an optical-axial direction, the third lens group includes, from the object side to the image side, a front group and a rear group,
the front group includes a cemented lens having a positive refractive power or includes a single lens having a positive refractive power, the rear group includes a cemented lens having a positive refractive power, and
the following conditional expressions (1) and (2) are satisfied:

$$0.45 < d3t/f32 < 0.8 \quad (1), \text{ and}$$

$$1.2 < f31/f32 < 5.0 \quad (2),$$

where,
d3t denotes a distance on an optical axis from a lens surface positioned nearest to an object in the front group up to a lens surface positioned nearest to the object in the rear group,
f32 denotes a focal length of the rear group, and
f31 denotes a focal length of the front group.

2. The objective optical system according to claim 1, wherein the following conditional expression (3) is satisfied:

$$0.28 < d3p/f32 < 0.5 \quad (3),$$

where,
d3p denotes a distance on the optical axis from a lens surface positioned nearest to an image in the front group up to the lens surface positioned nearest to the object in the rear group.

3. The objective optical system according to claim 1, wherein the following conditional expression (4) is satisfied:

$$2.3 < f3/f < 3.2 \quad (4),$$

where,
f3 denotes a focal length of the third lens group, and
f denotes a focal length of the objective optical system at a time of normal observation.

4. The objective optical system according to claim 1, wherein the second lens group has a positive refractive power.

5. An endoscope comprising:
an objective optical system; and
an image sensor;
wherein the objective optical system comprises in order from an object side to an image side:
a first lens group having a negative refractive power;
a second lens group; and
a third lens group having a positive refractive power,
wherein:
at a time of focusing, the second lens group moves in an optical-axial direction,
the third lens group includes, from the object side to the image side, a front group and a rear group,
the front group includes a cemented lens having a positive refractive power or includes a single lens having a positive refractive power,
the rear group includes a cemented lens having a positive refractive power, and
the following conditional expressions (1) and (2) are satisfied:

$$0.45 < d3t/f32 < 0.8 \quad (1), \text{ and}$$

$$1.2 < f31/f32 < 5.0 \quad (2),$$

where,
d3t denotes a distance on an optical axis from a lens surface positioned nearest to an object in the front group up to a lens surface positioned nearest to the object in the rear group,
f32 denotes a focal length of the rear group, and
f31 denotes a focal length of the front group.

6. The endoscope according to claim 5, wherein, in the objective optical system, the following conditional expression (3) is satisfied:

$$0.28 < d3p/f32 < 0.5 \quad (3),$$

where,
d3p denotes a distance on the optical axis from a lens surface positioned nearest to an image in the front group up to the lens surface positioned nearest to the object in the rear group.

7. The endoscope according to claim 5, wherein, in the objective optical system, the following conditional expression (4) is satisfied:

$$2.3 < f3/f < 3.2 \quad (4),$$

where,
f3 denotes a focal length of the third lens group, and
f denotes a focal length of the objective optical system at a time of normal observation.

8. The endoscope according to claim 5, wherein, in the objective optical system, the second lens group has a positive refractive power.

* * * * *